(12) United States Patent
Skinner et al.

(10) Patent No.: US 9,734,283 B2
(45) Date of Patent: Aug. 15, 2017

(54) GENOMIC FEATURES ASSOCIATED WITH EPIGENETIC CONTROL REGIONS AND TRANSGENERATIONAL INHERITANCE OF EPIMUTATIONS

(71) Applicant: Washington State University Research Foundation, Pullman, WA (US)

(72) Inventors: Michael K. Skinner, Pullman, WA (US); Carlos M. Guerrero-Bosagna, Pullman, WA (US)

(73) Assignee: Washington State University, Pullman, WA (US)

( * ) Notice: Subject to any disclaimer, the term of this patent is extended or adjusted under 35 U.S.C. 154(b) by 852 days.

(21) Appl. No.: 13/729,175

(22) Filed: Dec. 28, 2012

(65) Prior Publication Data
US 2013/0226468 A1 Aug. 29, 2013

Related U.S. Application Data

(60) Provisional application No. 61/581,932, filed on Dec. 30, 2011.

(51) Int. Cl.
C12Q 1/68 (2006.01)
G06F 19/22 (2011.01)
G06F 19/18 (2011.01)

(52) U.S. Cl.
CPC ........... *G06F 19/22* (2013.01); *C12Q 1/6827* (2013.01); *C12Q 1/68* (2013.01); *C12Q 1/6869* (2013.01); *G06F 19/18* (2013.01)

(58) Field of Classification Search
None
See application file for complete search history.

(56) References Cited

U.S. PATENT DOCUMENTS

| 2003/0100528 A1* | 5/2003 | Nicolas | A01K 67/0275 514/44 R |
| 2004/0097439 A9* | 5/2004 | Nicolas | A01K 67/0275 514/44 R |
| 2010/0234242 A1* | 9/2010 | Petronis | C12Q 1/6883 506/10 |
| 2012/0221249 A1* | 8/2012 | Lizardi | C12Q 1/6827 702/19 |

OTHER PUBLICATIONS

Butcher et al. (Methods (2010) vol. 52:223-231; available online on Apr. 10, 2010).*
Guerrero-Bosagna et al. (PLoS One (2010) vol. 5(9):e13100, pp. 1-17.*
Brinkman et al. (Methods (2010) vol. 52:232-236).*
Irizarry et al. (Nature Genetics (2009) vol. 41:178-186).*
Mohn et al. (Trends in Genetics (2009) vol. 25:129-136).*
Rauch et al. (Methods (2010) vol. 52:213-217).*
Skinner et al. (Trends in Endocrinology and Metabolism (2010) vol. 21:214-222).*
Skinner et al. (BMC Genomics (2014) vol. 15:692-6970.*
Thirlwell et al. (Clinical Epigenetics (2011) vol. 3:1-9).*
Anway et al. (Science (2005) vol. 308:1466-1469, plus erratum).*
Irizarry et al. (Nat. Genet (2009) vol. 41(2):178-186).*

* cited by examiner

*Primary Examiner* — Lori A Clow
(74) *Attorney, Agent, or Firm* — Whitham, Curtis & Cook, P.C.

(57) ABSTRACT

CpG densities and sequence motifs that are characteristic of regions of DNA associated with epimutations and control of epimutations are provided. Such regions include, within approximately 400 (or fewer) base pairs, at least one, usually two, and preferably all three of the following features: i) a CpG density of 15% or less; ii) the presence of the sequence motif ATTTGTTTTTTCTTTTnT (SEQ ID NO: 1) where n is A, T, C or G, and statistically relevant variants thereof; and iii) the presence of the sequence motif GGGGGnGGGG (SEQ ID NO: 2), where n is A, T, C or G, and statistically relevant variants thereof.

4 Claims, 25 Drawing Sheets

| Gene symbol | Description | MGI ID | Entrez gene ID | Significance (p ≤) | Changed region coordinates | | | Region size (bp) |
|---|---|---|---|---|---|---|---|---|
| | | | | | Chr | Start | End | |
| REGIONS WITH MeDIP CHANGE IN METHYLATION CONFIRMED BY REAL TIME qPCR VALIDATION | | | | | | | | |
| 2310005E10Rik | Aldo-keto reductase family 1, member B10 | 1915111 | 67861 | 5.61E-10 | 6 | 34333365 | 34334132 | 767 |
| 5730403M16Rik | RIKEN cDNA 5730403M16 gene | 1917764 | 108761 | 1.64E-08 | 7 | 7074813 | 7075523 | 710 |
| Arl6ip4 | ADP-ribosylation factor-like 6 interacting protein 4 | 1929500 | 65105 | 4.41E-08 | 5 | 124564910 | 124565615 | 705 |
| Cdca5 | Cdca5 cell division cycle associated 5 | 1915099 | 67849 | 2.65E-09 | 19 | 6082300 | 6082900 | 600 |
| Ceacam-ps1 | Carcinoembryonic antigen-related cell adhesion molecule pseudogene 1 | 3610557 | 100038912 | 4.18E-17 | 7 | 17243020 | 17244459 | 1439 |
| Cwc22 | CWC22 spliceosome -associated protein homolog to S. cerevisiae | 2136773 | 80744 | 1.46E-16 | 2 | 77783335 | 77785070 | 1735 |
| Dcxr | Dicarbonyl L-xylulose reductase | 1915130 | 67880 | 1.16E-13 | 11 | 120588514 | 120591382 | 2868 |
| Dhrs7 | Dehydrogenase/reductase (SDR family) member 7 | 1913625 | 66375 | 1.42E-09 | 12 | 73768059 | 73768659 | 600 |
| Egam-1c | Egam-1C | Predicted | 100047130 | 2.00E-08 | 7 | 16486685 | 16487477 | 792 |
| Elac1 | ElaC homolog 1 to E. coli | 1890495 | 114615 | 1.26E-08 | 18 | 73914746 | 73915346 | 600 |
| Elf3 | E74-like factor 3 | 1101781 | 13710 | 1.16E-18 | 1 | 137155288 | 137156184 | 896 |
| Eml1 | Echinoderm microtubule associated protein like 1 | 1915769 | 68519 | 2.30E-18 | 12 | 109646493 | 109647304 | 811 |
| Etv1 | Ets variant gene 1 | 99254 | 14009 | 2.75E-08 | 12 | 39504286 | 39505086 | 800 |
| Gdf2 | Growth differentiation factor 2 | 1321394 | 12165 | 9.77E-09 | 14 | 34751904 | 34752614 | 710 |
| Guca1a | Guanylate cyclase activator 1a (retina) | 102770 | 14913 | 9.73E-10 | 17 | 47537921 | 47538521 | 600 |
| Hoxb2 (region2) | Homeobox B2 | 96183 | 103889 | 9.46E-08 | 11 | 96211360 | 96211960 | 600 |
| Hsf1 or Bop1 | Heat shock factor 1 or Block of proliferation 1 | 96238 or 1334460 | 15499 or 12181 | 5.73E-08 | 15 | 76305346 | 76306056 | 710 |
| Il22 | Interleukin 22 | 1355307 | 50929 | 1.17E-08 | 10 | 117641731 | 117642331 | 600 |
| Itgb3 | Integrin beta 3 | 96612 | 16416 | 2.49E-10 | 11 | 104468315 | 104469310 | 995 |

*Figure 1A*

| Gene symbol | Description | MGI ID | Entrez gene ID | Significance (p ≤) | Changed region coordinates | | | Region size (bp) |
|---|---|---|---|---|---|---|---|---|
| | | | | | Chr | Start | End | |
| Krt78 | Keratin 78 | 1917529 | 332131 | 1.98E-08 | 15 | 101785650 | 101786540 | 890 |
| Krtap1-4 | 1-4 keratin associated protein 1-4 | 3651229 | 629873 | 1.36E-13 | 11 | 99444032 | 99444716 | 684 |
| Lif | Leukemia inhibitory factor | 96787 | 16878 | 6.57E-10 | 11 | 4164487 | 4165167 | 680 |
| Mro | Maestro | 2152817 | 71263 | 1.52E-15 | 18 | 74017620 | 74018584 | 964 |
| Ndufa8 | NADH dehydrogenase (ubiquinone) 1 alpha subcomplex, 8 | 1915625 | 68375 | 8.10E-10 | 2 | 35903161 | 35903761 | 600 |
| Nfe2l1 | Nuclear factor, erythroid derived 2, -like 1 | 99421 | 18023 | 1.06E-09 | 11 | 96692937 | 96693537 | 600 |
| Nkx6-3 | NK6 homeobox 3 | 1921811 | 74561 | 2.09E-08 | 8 | 24262064 | 24262664 | 600 |
| Olfr631 | Olfactory receptor 631 | 3030465 | 258961 | 9.82E-08 | 7 | 111061151 | 111061751 | 600 |
| Olfr978 | Olfactory receptor 978 | 3030812 | 259109 | 4.47E-09 | 9 | 39801429 | 39802029 | 600 |
| Pibf1 or Dis3 | Progesterone immunomodulatory binding factor 1 or DIS3 mitotic control homolog (S. cerevisiae) | 1261910 or 1919912 | 52023 or 72662 | 9.20E-09 | 14 | 99501070 | 99501670 | 600 |
| Plekhg3 | Pleckstrin homology domain containing, family G (with RhoGef domain) member 3 | 2388284 | 263406 | 5.19E-13 | 12 | 77632633 | 77633532 | 899 |
| Pelo | Pelota homolog to Drosophila | 2145154 | 105083 | 2.86E-15 | 13 | 115880977 | 115881882 | 905 |
| Prelid1 | PRELI domain containing 1 | 1913744 | 66494 | 2.06E-08 | 13 | 55425815 | 55426415 | 600 |
| Reg1 | Regenerating islet-derived 1 | 97895 | 19692 | 2.53E-09 | 6 | 78376091 | 78376691 | 600 |
| Sepn1 | Selenoprotein N, 1 | 2151208 | 74777 | 6.90E-09 | 4 | 134107080 | 134107680 | 600 |
| Sepw1 | Selenoprotein W, muscle 1 | 1100878 | 20364 | 6.75E-10 | 7 | 16509250 | 16510855 | 1605 |
| Skap1 | Src family associated phosphoprotein 1 | 1925723 | 78473 | 4.03E-22 | 11 | 96324250 | 96325444 | 1194 |
| Slc35b1 | Solute carrier family 35, member B1 | 1343133 | 110172 | 1.89E-12 | 11 | 95243522 | 95244222 | 700 |
| Slmo2 | Slowmo homolog 2 to Drosophila | 1913640 | 66390 | 3.36E-09 | 2 | 174299251 | 174300078 | 827 |
| St3gal2 | ST3 beta-galactoside alph a-2,3-sialyltransferase 2 | 99427 | 20444 | 9.64E-09 | 8 | 113440826 | 113441426 | 600 |
| Utp3 | UTP3, small subunit (SSU) processome component, homolog to S. cerevisiae | 1919230 | 65961 | 3.70E-11 | 5 | 88982036 | 88982731 | 695 |

*Figure 1B*

| Gene symbol | Description | MGI ID | Entrez gene ID | Significance (p ≤) | Changed region coordinates | | | Region size (bp) |
|---|---|---|---|---|---|---|---|---|
| | | | | | Chr | Start | End | |
| REGIONS WITH MeDIP CHANGE IN METHYLATION NOT ABLE TO BE TESTED WITH REAL TIME qPCR | | | | | | | | |
| 1700123K08Rik | RIKEN cDNA 1700123K08 gene | 1923908 | 76658 | 3.87E-20 | 5 | 139004928 | 139005608 | 680 |
| 4930579J09Rik | RIKEN cDNA 4930579J09 gene | 1915002 | 67752 | 1.38E-08 | 19 | 10559804 | 10560404 | 600 |
| AK053193 (region1) | RIKEN cDNA E03 0030I06 gene | 2442914 | 319887 | 1.23E-08 | 10 | 21869265 | 21869865 | 600 |
| Alx3 | Aristaless-like homeobox 3 | 1277097 | 11694 | 6.35E-08 | 3 | 107399690 | 107400290 | 600 |
| gm6485 | Predicted gene | 3644007 | 624251 | 4.00E-10 | 3 | 104555956 | 104556734 | 778 |
| Hoxb2 (region1) | Homeobox B2 | 96183 | 103889 | 3.27E-08 | 11 | 96209827 | 96210427 | 600 |
| Il1tifb | Interleukin 10-related T cell-derived inducible factor beta | 2151139 | 116849 | 2.54E-15 | 10 | 117732106 | 117732880 | 774 |
| Lrrc61 | Leucine rich repeat containing 61 | 2652848 | 243371 | 7.86E-23 | 6 | 48503482 | 48504082 | 600 |
| Pcdha4 | Protocadherin alpha 4 | 1298406 | 12936 | 1.85E-10 | 18 | 37113813 | 37114413 | 600 |
| Rpl31 | Ribosomal protein L31 | 2149632 | 114641 | 1.11E-12 | 1 | 39424522 | 39425122 | 600 |

*The criteria for a qChip value to be considered as a change are:
i) change is at least 1.2 fold increase or decrease regarding to control samples,
ii) passed t-test with p<0.05,
iii) trend of the change observed in qChip is the same as observed in the Me-Dip Chip array.

*Figure 1C*

| Gene Symbol | Gene name | Gene ID | Region changed | MeDIP-qPCR exposure/control ratio | | | |
|---|---|---|---|---|---|---|---|
| | | | | Plastics | Dioxin | Pesticide | Jet Fuel |
| Carm1 | Coactivator-associated arginine methyltransferase 1 | 363026 | chr8:20650587-20651612 | | | 3.696 | |
| Dmpk or Six5 | Dystrophia myotonica-protein kinase or SIX homeobox 5 | 308405 or 308406 | chr1:78450272-78451687 | 3.611 | | 2.658 | |
| Fgf15 | Fibroblast growth factor 15 | 170582 | chr1:205323456-205324556 | 25.688 | | | |
| Flg | Filaggrin | 24641 | chr2:186309317-186310200 | | 3.097 | 3.883 | |
| Hoxb6 | Homeo box B6 | 497986 | chr10:85032294-85033194 | 2.076 | | | |
| Hspd1 | Heat shock protein 1 (chaperonin) | 63868 | chr9:53896237-53896837 | | 0.696 | | |
| Irx2 | Iroquois homeobox 2 | 306657 | chr17:746309-746989 | | | 2.054 | |
| Nras | Neuroblastoma ras oncogene | 24605 | chr2:198292829-198293429 | | 7.986 | 9.022 | |
| Ntng1 | Netrin G1 | 295382 | chr2:205805922-205806522 | 0.13 | | | |
| Prrt1 | Proline-rich transmembrane protein 1 | 406167 | chr20:4220107-4221198 | | | 3.785 | |
| Rhoq | Ras homolog gene family, member Q | 85428 | chr6:10413845-10414445 | | | | 3.142 |
| Satb2 | SATB homeobox 2 | 501145 | chr9:55824749-55825838 | | | 0.114 | |
| Sema3b | Sema domain, immunoglobulin domain (Ig), short basic domain, secreted, (semaphorin) 3B | 363142 | chr8:112852022-112852622 | | 2.477 | | 2.48 |
| Shc2 | SHC (Src homology 2 domain containing) transforming protein 2 | 314612 | chr7:11584014-11584614 | | 2.081 | | |
| Tbx2 | T-box 2 | 303398 | chr10:74084425-74085225 | 5.776 | | | |
| Vom2r69 | Vomeronasal 2 receptor, 69 | 289433 | chr14:740492-741794 | | | | 0.517 |

*Figure 10A*

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Synthetic consensus sequence
<220> FEATURE:
<221> NAME/KEY: misc_feature
<222> LOCATION: (17)..(17)
<223> OTHER INFORMATION: n = A, T, C, or G

<400> SEQUENCE: 1
atttgttttt tcttttnt                                                  18

<210> SEQ ID NO 2
<211> LENGTH: 10
<212> TYPE: DNA
<213> ORGANISM: Artificial Sequence
```

```
<220> FEATURE:
<223> OTHER INFORMATION: Synthetic consensus sequence
<220> FEATURE:
<221> NAME/KEY: misc_feature
<222> LOCATION: (6)..(6)
<223> OTHER INFORMATION: n = A, T, C, or G

<400> SEQUENCE: 2 gggggngggg                                                                        10
```

GENOMIC FEATURES ASSOCIATED WITH EPIGENETIC CONTROL REGIONS AND TRANSGENERATIONAL INHERITANCE OF EPIMUTATIONS

CROSS-REFERENCE TO RELATED APPLICATIONS

This application claims benefit of U.S. provisional patent application 61/581,932, filed Dec. 30, 2011, the complete contents of which is hereby incorporated by reference.

SEQUENCE LISTING

This application includes as the Sequence Listing the complete contents of the accompanying text file "Sequence.txt", created Dec. 20, 2012, containing 894 bytes, hereby incorporated by reference.

BACKGROUND OF THE INVENTION

Field of the Invention

The invention generally relates to the identification of epigenetic modification and/or epigenetic regulatory regions of DNA that are associated with the transgenerational inheritance of epimutations. In particular, the invention provides sequence features (e.g. CpG density levels and sequence motifs) that are characteristic of, and can thus be used to identify, such regions.

Background of the Invention

The current paradigm for the etiology of heritable diseases, including those caused by environmental insult, is based primarily on mechanisms of genetic alterations such as DNA sequence mutations. However, the majority of inherited diseases have not been linked to specific genetic abnormalities or changes in DNA sequence. In addition, the majority of environmental factors known to cause or influence the development of disease—including heritable diseases—do not have the capacity to alter DNA sequence.[1, 2] Therefore, additional molecular mechanisms need to be taken into account when attempting to clarify the etiology of diseases and to develop diagnostic tools and treatments.

SUMMARY OF THE INVENTION

The present invention reflects the realization that many diseases, even those which are passed from parent to offspring, are not caused by genetic mutations. Rather, the causes of these diseases can be traced to epigenetic modifications of the genome. An embodiment of the invention provides methods of identifying regions of DNA which are likely to harbor and/or regulate such epigenetic modifications. These regions of DNA are characterized by the presence of at least one, usually two, and preferably all three of the following features: i) a CpG density of 15% or less; ii) the presence of at least one DNA sequence motif ATTTGTTTTTCTTTTnT (SEQ ID NO: 1, also referred to as "EDM1"), where n is A, T, C or G, and/or statistically relevant degenerate forms thereof; and iii) the presence of at least one DNA sequence motif GGGGGnGGGG (SEQ ID NO: 2, also referred to as "EDM2"), where n is A, T, C or G, and/or statistically relevant degenerate forms thereof. It has been discovered that these features are hallmarks or indicators of epigenetic control regions (ECRs), and provide investigators with a means to search DNA sequences in order to locate or identify likely ECRs. ECRs identified in this manner may be employed, for example, in diagnostic assays as indicators of the presence of or susceptibility to epigenetic modification(s) in a subject. It is noted that the discovery of the association between low CpG content and ECRs is contrary to prior conventional thinking in the art, which has focused instead on regions of high CpG content, e.g. "CpG islands".

Embodiments of the invention provide computer-implemented methods of identifying potential genomic locations and regulatory sites of epimutations. In one embodiment, the method comprises the steps of: a) inputting into a computer at least one genomic DNA sequence; b) identifying, with said computer, one or more regions of said at least one genomic DNA sequence which comprise one or both of the following: i) at least one DNA sequence region with a low density of CpG; and ii) at least one DNA sequence motif that is associated with one or both of epimutations and regulatory sites of epimutations. The one or more regions are determined to be or to contain one or both of the following: I) potential locations of epimutations, and II) potential regulatory sites of epimutations. In some embodiments, the one or more regions of said at least one genomic DNA sequence are at least 400 base pairs long. In some embodiments, the low density of CpG is 15% or less CpG. In yet other embodiments, the at least one DNA sequence motif is EDM1. In other embodiments, the at least one DNA sequence motif is EDM2.

Other embodiments of the invention provide computer-implemented methods of identifying potential genomic locations and regulatory sites of epimutations, the methods comprising the steps of: i) inputting into a computer at least one genomic DNA sequence; and ii) identifying, with the computer, one or more regions of the at least one genomic DNA sequence which comprise (include, contain) at least one nucleotide sequence with a low density of CpG. The one or more regions are determined to be or contain one or both of a) potential locations of epimutations and b) potential regulatory sites of epimutations. In some embodiments, the one or more regions of the at least one genomic DNA sequence are at least 400 base pairs long. In other embodiments, the low density of CpG is less than 15% CpG. In yet other embodiments, the one or more regions of the at least one genomic DNA sequence are at least 400 base pairs long. Other embodiments further comprise the step of, with the computer, identifying, within the one or more regions of the at least one genomic DNA sequence, at least one DNA sequence motif that is associated with one or both of epimutations and regulatory sites of epimutations. The DNA sequence motif may be, for example EDM1 or EDM2.

Other embodiments of the invention provide computer-implemented methods of identifying potential genomic locations and regulatory sites of epimutations, comprising the steps of i) inputting into a computer at least one genomic DNA sequence; and ii) identifying, with the computer, one or more regions of the at least one genomic DNA sequence which comprise at least one EDM2 DNA sequence motif. The one or more regions are determined to be or contain one or both of potential locations of epimutations and potential regulatory sites of epimutations. The one or more regions of the at least one genomic DNA sequence may further comprise at least one region of low density CpG. In some embodiments, the one or more regions of the at least one genomic DNA sequence further comprise at least one EDM1 DNA sequence motif.

Further embodiments of the invention provide computer-implemented methods of diagnosing, prognosticating and/or monitoring therapeutic responsiveness (e.g. to a drug or other treatment regimen) in (of) a subject in need thereof, comprising the steps of i) inputting into a computer at least one genomic DNA sequence from the subject; ii) identifying, with the computer, one or more regions of the at least one genomic DNA sequence which comprises nucleotide sequences associated with one or both of epimutations and regulatory sites of epimutations, where the one or more regions are determined to be or to contain one or both of potential locations of epimutations and potential regulatory sites of epimutations; and iii) determining the presence or absence of an epigenetic modification within the one or more regions of genomic DNA in the subject, wherein the presence or absence of the epigenetic modification is indicative of (associated with, correlated with, etc.) the therapeutic responsiveness of the subject. For example, if the epigenetic modification is present, the subject may (or may not) be likely respond to the treatment; and if the epigenetic modification is absent, the subject may (or may not) be likely to respond to the treatment. In some embodiments, the one or more regions of the at least one genomic DNA sequence comprise one or both of i) at least one region of low density CpG; and ii) at least one DNA sequence motif that is associated with one or both of epimutations and regulatory sites of epimutations.

In other embodiments, the invention provides systems comprising i) a computer; ii) at least one non-transient storage medium comprising computer executable instructions which are performed by the computer and which cause the computer to carry out the steps of a) receiving at least one genomic DNA sequence as input; b) scanning the at least one genomic DNA sequence in order to identify regions of the at least one genomic DNA sequence which comprise at least one nucleotide sequence with a low density of CpG; and c) scanning the at least one genomic DNA sequence in order to identify at least one DNA sequence motif that is associated with one or both of epimutations and regulatory sites of epimutations; and iii) an output device capable of presenting results obtained by the computer in one or both of the scanning steps. In some embodiments, the at least one non-transient storage medium further comprises instructions for causing the computer to receive the at least one genomic DNA sequence from a nucleotide sequencing apparatus. In other embodiments, the at least one non-transient storage medium further comprises instructions for causing the computer to receive the at least one genomic DNA sequence from a database. In some embodiments, the low density of CpG is less than 15% CpG. In other embodiments, the regions of the at least one genomic DNA sequence are at least 400 base pairs long. In yet other embodiments, the at least one DNA sequence motif that is associated with one or both of epimutations and regulatory sites of epimutations is selected from the group consisting of EDM1 and EDM2.

BRIEF DESCRIPTION OF THE DRAWINGS

FIG. 1A-C. Description and annotation of the regions showing vinclozolin-induced transgenerational change in F3 generation sperm with MeDip-Chip. Some of the regions were confirmed with Real Time qPCR validation on MeDIP material. For other regions appropriate primers could not be optimized for the region interrogated.

DETAILED DESCRIPTION

Figure 2A:
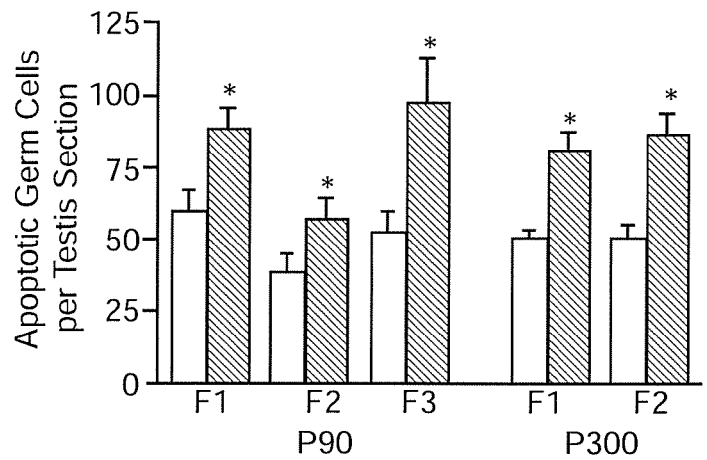
FIG. 2A-E. Testicular spermatogenic cell apoptosis in (a) 129 mouse strain vinclozolin lineage, (b) 129 mouse strain flutamide lineage, and (c) CD-1 mouse strain vinclozolin lineage. The mean±SEM for control (open bars) and treated lineage (closed bars). The CD-1 mouse vinclozolin lineage treatment of V1 (black bar) and V2 (gray bar) is presented. No significant difference in tubule cross section numbers was detected between treatment lineages or treatments. The asterisks (*) indicate a statistically significant difference with P<0.05. The visible apoptotic cells (TUNEL assay) for control (d) and treated (e) testes are presented.

Epigenetic regulatory sites and epigenetic mutation sites (such as those involving differential DNA methylation) have profound regulatory effects on gene expression, cell function and the development of abnormal physiology and disease. The presence of such sites in the germline (e.g. sperm) can promote epigenetic transgenerational inheritance of, e.g. adult onset disease. Therefore, identification of these epimutations and/or epigenetic control regions (referred to collectively herein as "epigenetic control regions" or "ECRs") is critical to understanding disease etiology and heritable conditions that do not follow classic Mendelian genetics, and to the diagnosis and treatment of such conditions. Accordingly, identifiable, detectable genomic features characteristic of ECRs and methods for their identification are described herein. The features, which permit the identification and subsequent use of ECRs, include: i) low density CpG, e.g. a CpG density of about 15% or less; ii) the presence of at least one DNA sequence motif ATTTGTTTTTTCTTTTnT (SEQ ID NO: 1), where n is A, T, C or G, and/or statistically relevant variant forms thereof; and iii) the presence of at least one sequence motif GGGGGnGGGG (SEQ ID NO: 2), where n is A, T, C or G, and/or statistically relevant variant forms thereof. These features, when occurring within a segment of DNA of a least 400 bps, indicate that the segment is or harbors one or both of an epimutation and/or an epigenetic control region. These genetic features of low density CpG and/or unique DNA sequence motifs can be used to facilitate the identification of epigenetic biomarkers which are used, for example, for the diagnosis of diseases characterized or caused by epigenetic modifications, to detect the occurrence of environmental exposure to an epigenetically active agent, to detect or predict the transgenerational inheritance of abnormal phenotypes, and for other purposes.

By "epigenetic control region" or "ECR" we mean a segment of DNA which is at least about 400 bp in length, and which is characterized by (contains, comprises, harbors, etc.) at least one, usually at least two, and most frequently all three of the features described herein i.e. CpG density of 15% or less, and the DNA sequence motifs described herein. As demonstrated herein, such DNA segments encompass at least one epimutation and/or at least one epimutation regulatory site. ECRs comprise at least about 400 contiguous base pairs, and may contain up to about 1000 bps (e.g. about 450, 500, 550, 600, 650, 700, 750, 800, 850, 900, 950 or more) base pairs. In some embodiments, the regions are even larger, e.g. about 1000 or more bps. One or more copies of each DNA sequence motif may be present in a region.

"Epimutation" and "epigenetic modification" as used herein refer to modifications of cellular DNA that affect gene expression without altering the DNA sequence. The epigenetic modifications are both mitotically and meiotically stable, i.e. after the DNA in a cell (or cells) of an organism has been epigenetically modified, the pattern of modification persists throughout the lifetime of the cell and is passed to progeny cells via both mitosis and meiosis. Therefore, with the organism's lifetime, the pattern of DNA modification and consequences thereof, remain consistent in all cells derived from the parental cell that was originally modified. Further, if the epigentically modified cell undergoes meiosis to generate gametes (e.g. eggs, sperm), the pattern of epigenetic modification is retained in the gametes and thus inherited by offspring. In other words, the patterns of epigenetic DNA modification are transgenerationally transmissiable or inheritable, even though the DNA nucleotide sequence per se has not been altered or mutated. Without being bound by theory, it is believed that enzymes known as methyltransferases shepherd or guide the DNA through the various phases of mitosis or meiosis, reproducing epigenetic modification patterns on new DNA strands as the DNA is replicated.

Exemplary epigenetic modifications include but are not limited to DNA methylation, histone modifications, chromatin structure modifications, and non-coding RNA modifications, etc.

Epigenetic modifications may be caused by exposure to any of a variety of factors, examples of which include but are not limited to: chemical compounds e.g. endocrine disruptors such as vinclozolin; chemicals such as those used in the manufacture of plastics e.g. bispheol A (BPA); bis(2-ethylhexyl)phthalate (DEHP); dibutyl phthalate (DBP); insect repellants such as N,N-diethyl-meta-toluamide (DEET); pyrethroids such as permethrin; various polychlorinated dibenzodioxins, known as PCDDs or dioxins e.g. 2,3,7,8-tetrachlorodibenzo-p-dioxin (TCDD); extreme conditions such as abnormal nutrition, starvation, etc.

In some embodiments, the practice of the invention involves determining the CpG density of segments of DNA (usually genomic DNA) that are at least about 400 bps in length. DNA segments found to have CpG densities of about 15% or less, e.g. about 14, 13, 12, 11, 10, 9, 8, 7, 6, 5, 4, 3, 2, or 1% or less, are deemed likely to contain at least one ECR. In other words, a value of 15% or less represents a threshold or trigger value for identifying genomic locations/regions of and/or regulatory sites of epimutations. With respect to detecting regions of low CpG density, those of skill in the art are familiar with techniques and methodologies for analyzing nucleotide sequences in order to determine the "content" or density (i.e. frequency) of a particular sequence, e.g. a dinucleotide sequence such as CpG. The methods may be linked to and used in conjunction with sequencing of a DNA molecule, or may be practiced in silico using a known sequence. Algorithms for carrying out such analyses are known and readily available. Those of skill in the art will recognize that the "%" of a sequence of interest (e.g. CpG) means that the sequence occurs the indicated number of times per 100 base pairs analyzed, e.g. 15% or less CpG means that the dinucleotide sequence C followed by G occurs at most 15 times per 100 base pairs within a DNA segment that is analyzed. Analyses are usually carried out by iterative analysis of consecutively overlapping sequences within a large DNA molecule of interest, e.g. a chromosome, a section of a chromosome, etc.

Figure 12A:
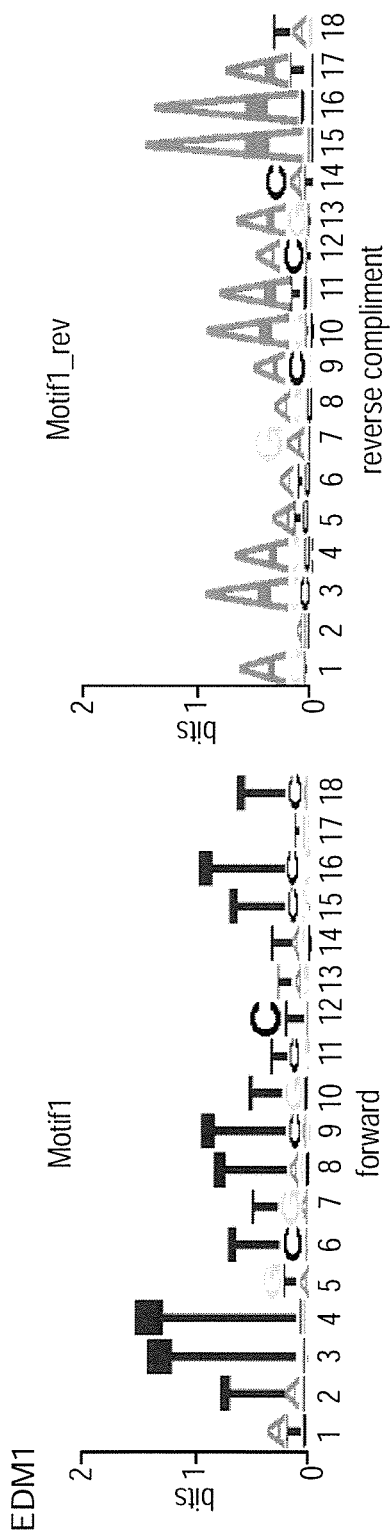
FIGS. 12A, B, C-1 to C4 and D. Schematic representation of forward and reverse complement sequences of the Environmentally Induced Differential Methylation (EDM) consensus motifs A, EDM1 (SEQ ID NO: 1) and B, EDM2 (SEQ ID NO: 2). The correlation analysis to create the concensus EDM2 motif is shown in C-1 through C-4. Examples of the presence of EDM1 and EDM2 in various differential DNA methylation regions (DMR) are shown in D.
Figure 12B:
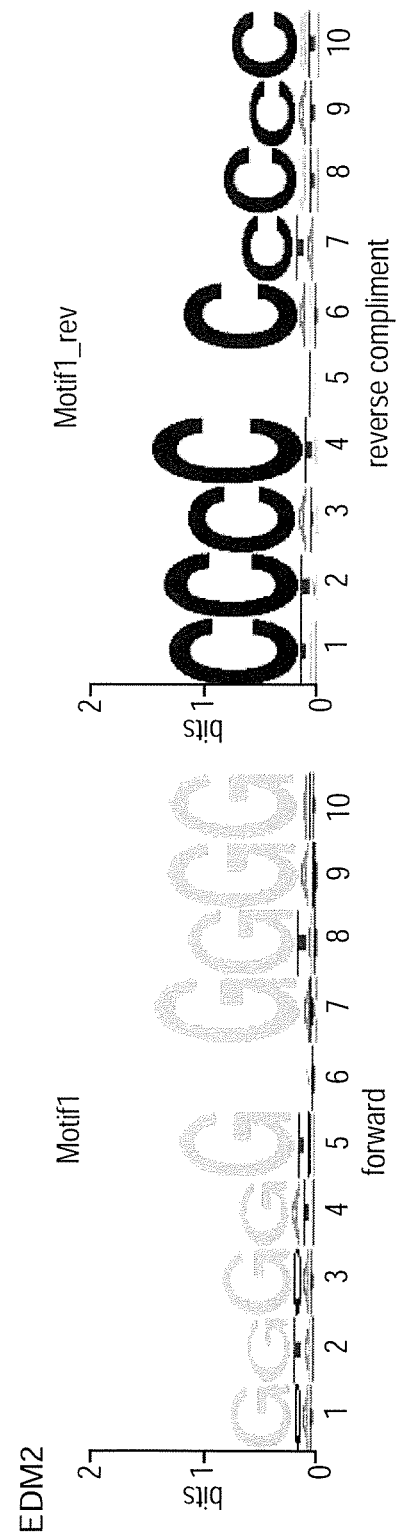
Figures 1, 12C:
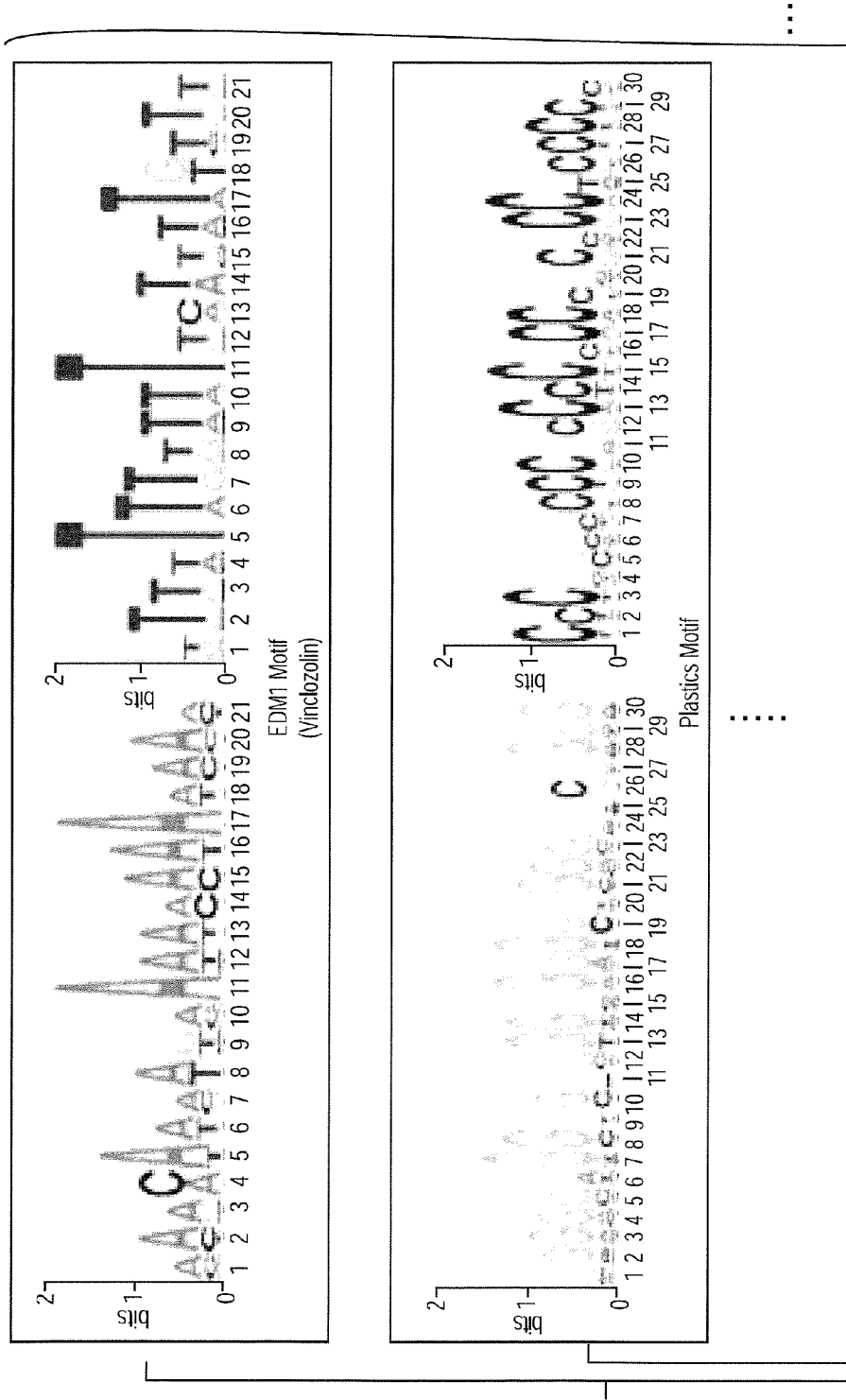
Figures 2, 12C:
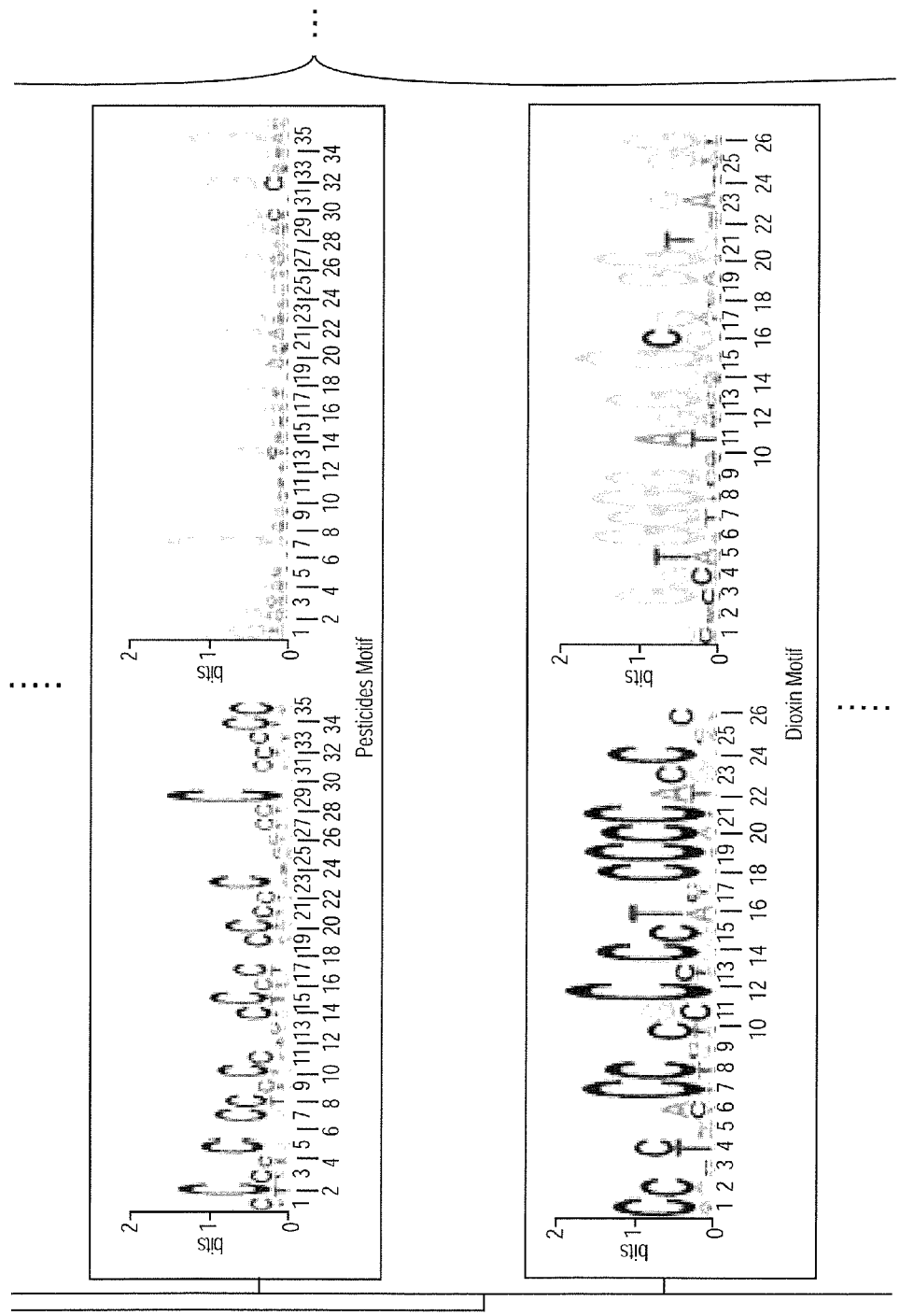
Figures 3, 12C:
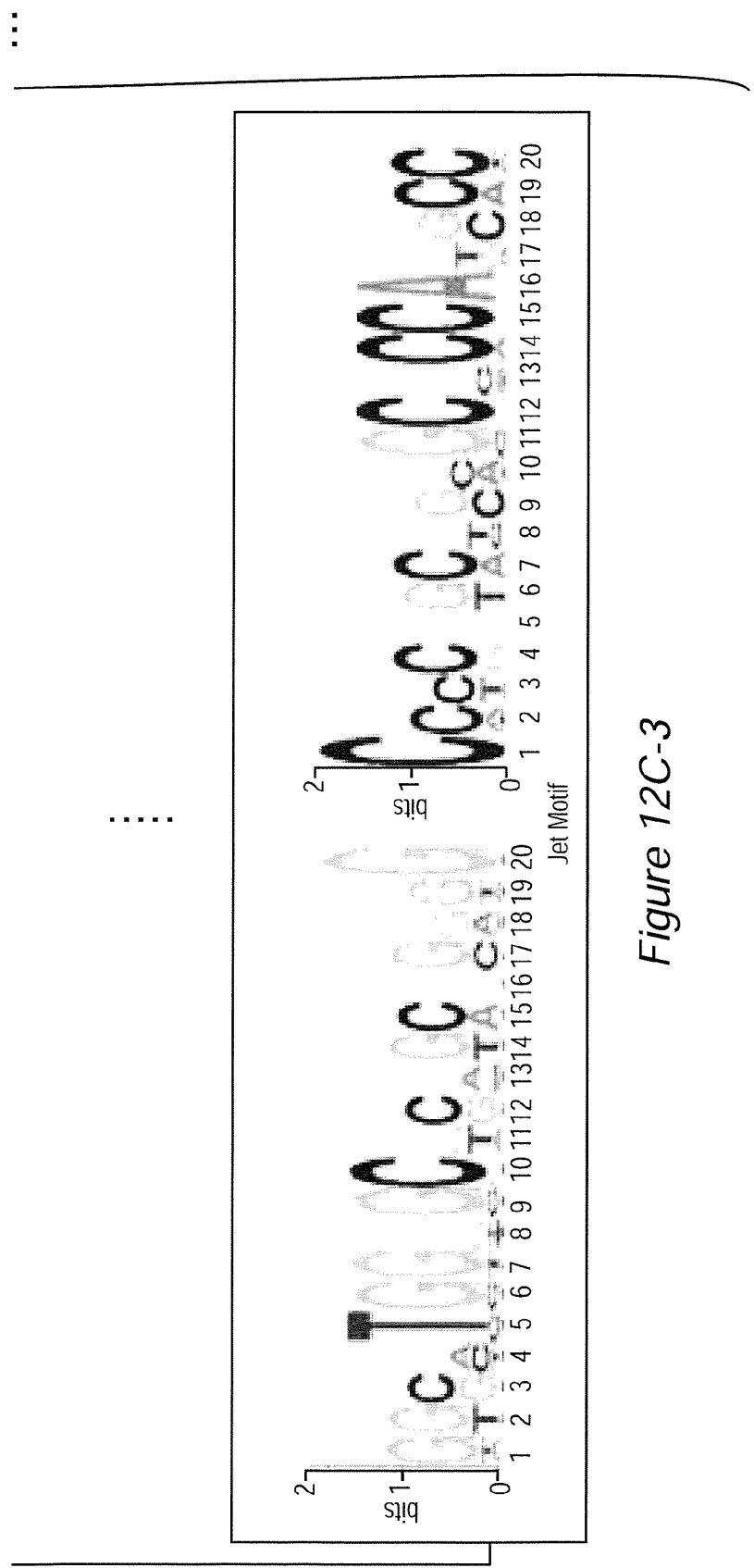
Figures 4, 12C:
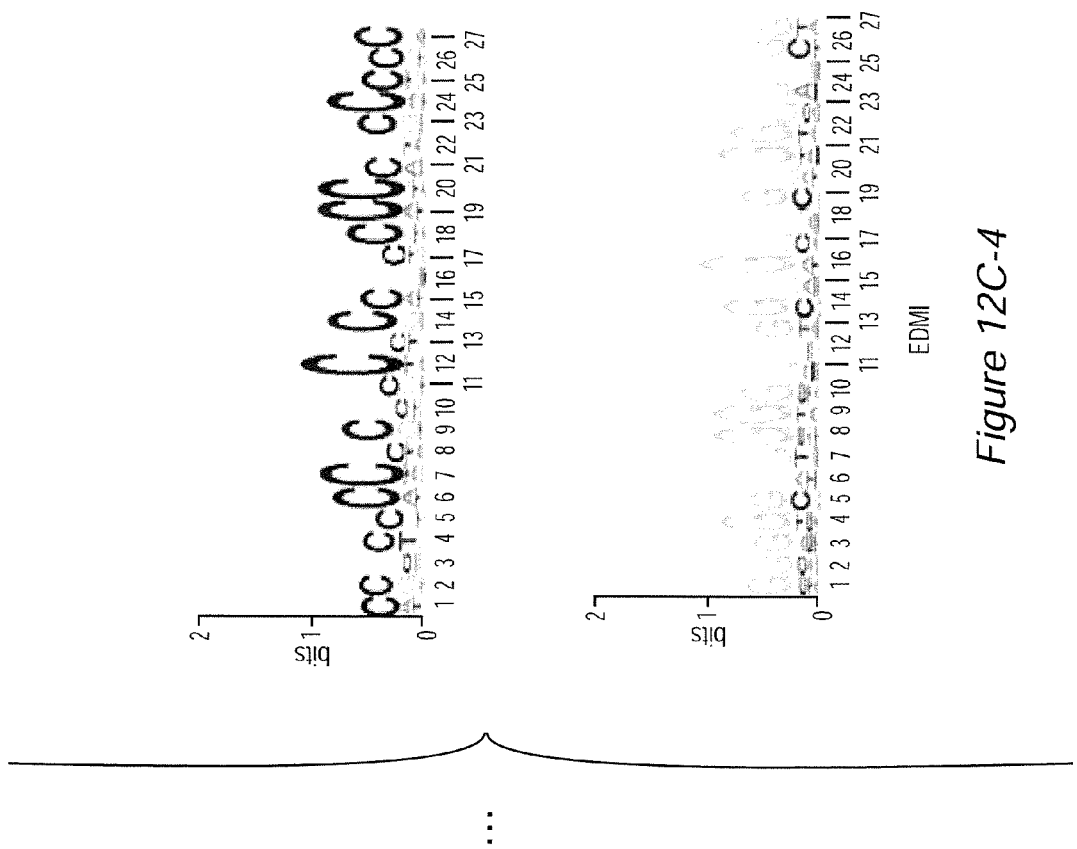
Figure 12D:
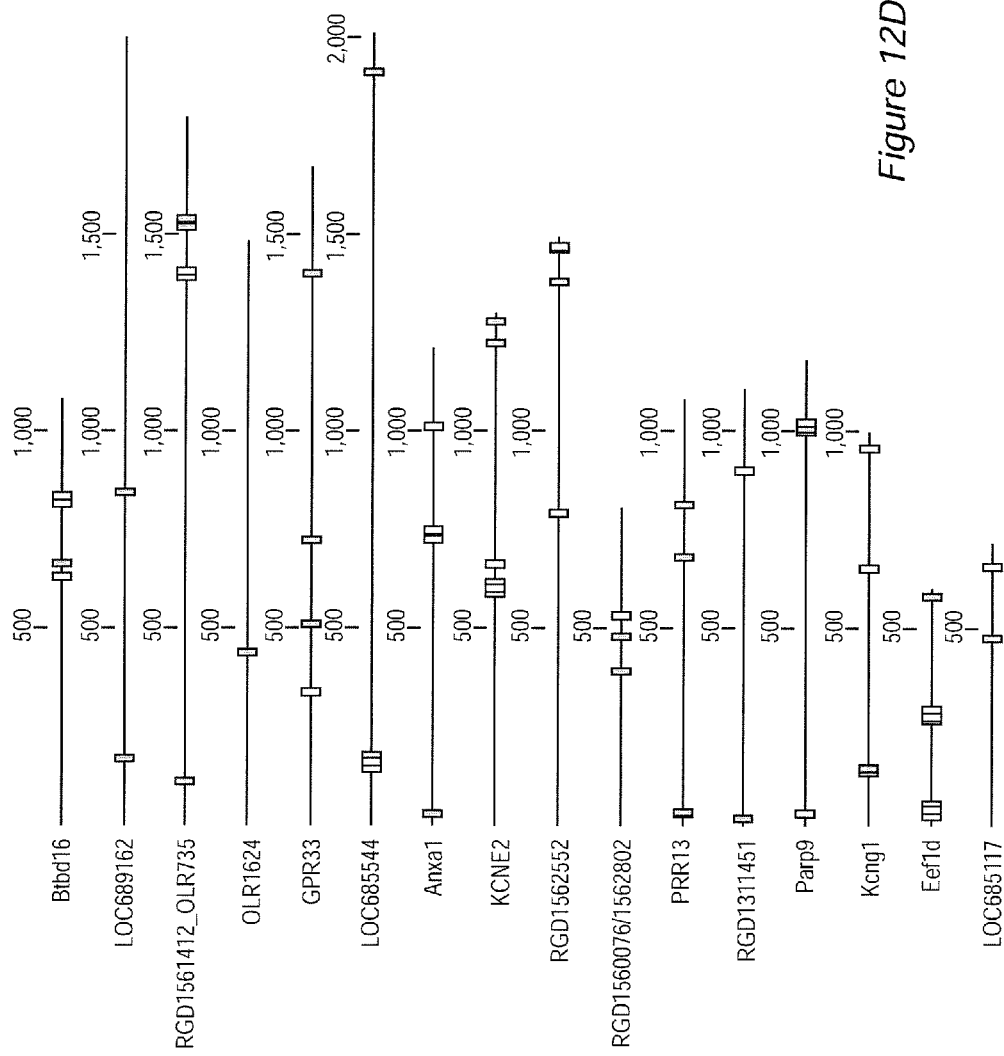

The DNA sequence motifs that are identified using the methods of the invention are depicted schematically in FIGS. 12A and B. EDM1 was previously identified (Guerrero-Bosagna et al, PloS ONE (2010), volume 5, issues 9). EDM1 is similar to but different from known transcription factors binding sites AZF1, FOXP1 and HMG-1Y. EDM2 is disclosed for the first time herein and is similar to but different from known transcription factor binding sites KROX, MAZ, UF1H3BETA, ZNF219 and SP1. The consensus sequences for EDM1 and EDM2 are presented in FIGS. 12A and B, where the preferred consensus is the top line (uppermost nucleotide) in the diagram. However, those of skill in the art will recognize that some statistically relevant variant forms of the motif may also be utilized. For example, EDM1 contains 18 bases, and position 1 is A but may also be T with nearly equal frequency; position 2 is usually T and less frequently may be A; position 5 is typically G but is almost as frequently G, etc. The same is true for the 10-bp EDM2, in which for example, positions 2, 5 and 8 are usually G but in some variants, one or more of these positions may be T. All variants of EDM1 and EDM2 which contain one or more of these alternate bases, as depicted in FIGS. 12A and B, are encompassed by the present invention. The correlations between DMR from different exposures that were used to generate the consensus EDM2 are shown in FIG. 12C. Examples of various DMR that contain EDM1 and EDM2 and the correlated chromosomal locations are shown in FIG. 12D. This demonstrates the correlation of these motifs in the specific differential DNA methylated regions.

Identification of the DNA sequence motifs described herein may be carried out by any suitable means known to those of skill in the art. Any algorithm or software program known to one skilled in the art may be used to identify statistically-enriched regions of DNA-sequence motifs within a genome of interest, or section thereof (e.g. particular chromosomes, particular loci, etc.). In some embodiments, sequences of interest are identified using one or more of the following programs or algorithms, as described in issued U.S. Pat. No. 7,611,838, the complete contents of which is hereby incorporated by reference in entirety: Gibbs Sampler (Rajewsky et al. (2002) BMC Bioinformatics, 3:30; Lawrence et al. (1993) Science, 262, 208-214.); R'MES programs (Schbath S, (1997) J. Comp. Biol., 4, 189-192), the Verbumculus program (Apostolico et al., (2000) Journal of Computational Biology, vol. 7, no. 1/2; Apostolico et al. (2004) Journal of Computer and Science Technology, vol. 19, no. 1, pp. 22-41), the YMF program (Sinha et al., (2002) Nucleic Acids Research, vol. 30, no. 24, 5549-5560, and Sinha et al. (2000) Eighth International Conference on Intelligent Systems for Molecular Biology, San Diego, Calif., 344-354); the AlignACE (Aligns Nucleic Acid Conserved Elements) (Hughes et al (2000), Journal of Molecular Biology; 296(5):1205-14, and Roth et al, (1998) Nature Biotechnology, 16(10):939-45, 1998), the BioProspector program (Liu X et al (2001) Pac. Symp. Biocomput., 127-38, the MEME program (Bailey et al (1994) Proceedings of the Second International Conference on Intelligent Systems for Molecular Biology, 28-36, AAAI Press); Motif Sampler (Thijs G (2001) et al. Bioinformatic, 17(12), 1113-1122, and Thijs G et al. Journal of Computational Biology (special issue Recomb'2001), 9(2), 447-464, 2002), and SUPERPOSITION (Shinozaki D et al., (2003) Bioinformatics; 19 Suppl 2:11206-11214). Also included are the Motif Discovery scan (MDscan) program (Liu X S et al. (2002) Nat. Biotechnol., 20(8):835-9) and the Mogul program, which incorporates multiple algorithms (Rust et al. Int. Conf. on Systems Biology (ISMB2003), 2003). Additional algorithms have also been described (see Bailey et al. (1994) Proc. Int. Conf. Intell. Syst. Mol. Biol., 2, 28-36. In some embodiments, more than one algorithm is used to identify the DNA-sequence motif.

In some embodiments, delineation of ECRs as described herein involves obtaining the nucleotide sequence of a selected DNA sequence of interest (e.g. by obtaining a DNA sample from a donor or subject and then sequencing the DNA within the sample; or obtaining a known nucleotide sequence from a database), and then analyzing the nucleotide sequence in order to determine whether or not one or more of the features characteristic of ECRs is present in the sequence of interest. Computer executable algorithms and software programs for implementing the same are also encompassed by the invention. Such software programs generally contain instructions for causing a computer to carry out the steps of the methods disclosed herein. The computer program will be embedded in a non-transient medium such as a hard drive, DVD, CD, thumb drive, etc.

As stated above, in some embodiments, the nucleotide sequence of the DNA sequence of interest may be unknown and it may be necessary to carry out a step of sequencing. Those of skill in the art are familiar with techniques that may be used to sequence DNA, including but not limited to: the Maxam-Gilbert chemical degradation method, the Sanger dideoxy chain termination technique, etc. DNA sequencing has been summarized in many review articles, e.g., B. Barrell, The FASEB Journal, 5, 40 (1991); and G. L. Trainor, Anal. Chem. 62, 418 (1990), and references cited therein. The most widely used DNA sequencing chemistry is the enzymatic chain termination method of Sanger, mentioned above, which has been adopted for several different sequencing strategies. The sequencing reactions are either performed in solution with the use of different DNA polymerases, such as the thermophilic Taq DNA polymerase [M. A. Innes, Proc. Natl. Acad. Sci. USA, 85: 9436 (1988)] or specially modified T7 DNA polymerase ("SEQUENASE") [S. Tabor and C. C. Richardson, Proc. Natl. Acad. Sci. USA, 84, 4767 (1987)], or in conjunction with the use of polymer supports. See for example S. Stahl et al., Nucleic Acids Res., 16, 3025 (1988); M. Uhlen, PCT Application WO 89/09282; Cocuzza et al., PCT Application WO 91/11533; and Jones et al., PCT Application WO 92/03575.

In other embodiments, the nucleotide sequences of the DNA sequence(s) of interest have already been determined and are retrieved e.g. from a database. Such databases, many of which are publically available, are well known to those of skill in the art, e.g. GenBank.

Selection of a DNA sequence of interest may be predicated on and/or influenced by any number of factors. For example, the DNA sequence of interest may be from a particular species under study (e.g. a mammalian species, including but not limited to humans); the DNA sequence of interest may be from a particular chromosome or region of a chromosome that is suspected to be involved in a disease or condition of interest; etc. The DNA sequence of interest may be isolated from a subject or subjects known or suspected to be afflicted with a disease or condition associated with epigenetic mutations; or who have been or are suspected of having been exposed to an agent that causes, or is suspected of causing, epigenetic mutations; or who have inexplicably inherited a disease or disease condition from a parent for which no DNA sequence mutation has been identified, etc. Subjects whose DNA is analyzed may be or any age or gender, and in any stage of development, so long as cells containing a DNA sequence of interest can be obtained from the subject. For example, the subject may be an adult, an adolescent, a child, an infant, an embryo, a laboratory animal, etc. The cells from which the DNA is obtained may be any suitable cell, including but not limited to gametes, cells from swabs such as buccal swabs, cells sloughed into amniotic fluid, etc.

The genomic features described herein may be used in a variety of therapeutic applications. For example, they may be used to identify locations of epigenetic modification, or locations that are susceptible to epigenetic modification, within a gene sequence of interest. The gene sequence of interest may be a chromosome or a region of interest within a chromosome. Once identified, such regions can serve as biomarkers to be used e.g. in disease diagnosis and/or to detect environmental exposures to agents or conditions that cause epimutations and/or to monitor therapeutic responsiveness to a medicament or treatment and/or used as prognostic indicators. For example, once a particular location on a chromosome is determined to be a region with a high incidence of epigenetic modifications associated with a particular disease or syndrome, or with exposure to a particular agent or event (e.g. exposure to dioxin), then subjects with or without symptoms of exposure can be screened using a diagnostic that detects epigenetic modification of the region. The detection of epigenetic modification at the region (i.e. a positive diagnostic result) will suggest or confirm that the subject has, indeed, likely been exposed to dioxin, and treatments suitable for dioxin exposure can be instituted. In contrast, a negative result (no epigenetic modification at the site) suggests that the subject has not been exposed to dioxin (or at least that the exposure did not result in damage), and other reasons for disease symptoms displayed by the subject can be investigated. If it is known that exposure did occur, then prophylactic screening of a DNA sample from a patient can result in early identification of a risk of disease and lead to early therapeutic intervention. In addition, ongoing monitoring of the extent of epigenetic modification of a site can provide valuable information regarding the outcome of the administration of agents (e.g. drugs or other therapies) which are intended to treat or prevent a condition caused by epimutation, i.e. the therapeutic responsiveness of a patient. Those of skill in the art will recognize that such analyses are generally carried out by comparing the results obtained using an unknown or experimental sample with results obtained a using suitable negative or positive controls, or both.

Information concerning the type and extent of epigenetic modification in a subject may be used in a variety of decision making processes undertaken by a subject that is tested. For example, depending on the severity of the symptoms caused by an epigenetic modification that is identified, a subject may decide to forego having children or to terminate a pregnancy in order to prevent transmission of the modification to offspring. Diagnostic tests based on the present invention can be included in prenatal testing.

In other embodiments, the regions identified as described herein may be monitored in order to ascertain whether or not administration or exposure to an agent or environmental stimulus causes epimutations. For example, candidate drugs or other treatments that are found to cause epigenetic modifications, for example, in cell or animal studies, or during clinical trials, might be avoided or used only as a last resort in a clinical setting, or rejected altogether as viable drug candidates.

Subjects whose DNA is analyzed may be suffering from any of a variety of disorders (diseases, conditions, etc.) including but not limited to: various known late or adult onset conditions, such as low sperm production, abnormalities of sexual organs, ovarian cysts, kidney abnormalities, prostate disease, immune abnormalities, behavioral effects, etc. In other embodiments, no symptoms are present but screening using the diagnostics is employed to rule out the presence of "silent" epigenetic mutations which could cause disease symptoms in the future, or which could be inherited and cause deleterious effects in offspring.

The regions that are identified as described herein may also be used to screen and identify therapeutic modalities for the treatment of epigenetic mutations. Those of skill in the art will recognize that such methods of screening are typically carried out in vitro, e.g. using a DNA sequence that is immobilized in a vessel, or that is present in a cell. However, such tests may also be carried out in model laboratory animals, once the regions are identified. In one embodiment, candidate agents which reverse epigenetic modification are screened by analyzing the regions. In another embodiment, candidate agents which prevent epigenetic modifications are screened by analyzing the regions. In this way, the epigenetic biomarkers can be used to facilitate, e.g. drug development and clinical trials patient stratification (i.e. pharmacoepigenomics).

The invention also provides a system for carrying out the methods of the invention. The system comprises, for example, i) a computer; and ii) non-transient storage medium comprising computer executable instructions which are performed by the computer and which cause the computer to carry out the steps of a) receiving at least one genomic DNA sequence as input; b) scanning said at least one genomic DNA sequence in order to identify regions of said genomic DNA which comprise at least one nucleotide sequence with a low density of CpG; and c) scanning said at least one genomic DNA sequence in order to identify at least one DNA sequence motif that is associated with epimutations and regulatory sites of epimutations. The system also generally comprises iii) an output device capable of presenting results obtained by the computer during or as a result of (e.g. in) scanning steps. The non-transient storage medium may be on the hard drive of the computer, or may be located on a portable device such as a disc, CD, DVD, thumb drive, flash drive, lap top, portable computer (e.g. a PC or other type), or other such device. Alternatively, the non-transient storage medium may be at a location such as a remote location or a database that is accessible via the internet, or stored in a cloud, or in or on another computer or computer system that is accessible by the computer of the system. The non-transient storage medium may also include instructions for causing the computer to receive, as input, at least one genomic DNA sequence from a nucleotide sequencing apparatus or from a database. The database may be downloaded from a remote site (e.g. via the internet), and/or may be located (stored) on the computer, or may be located on another computer or computer system that is accessible by the computer of the system, or may even be located on a portable device as described above. In other embodiments, the data is downloaded from a gene sequencing apparatus, and the system may also include such an apparatus. If present, the apparatus is operably electronically linked to the computer in a manner that allows data gathered or measured by the sequencing apparatus (e.g. a nucleotide sequence) to be outputted and transmitted to and received as input by the computer.

The computer can carry out the analysis of one genomic sequence at a time, or, in some embodiments, can analyze two or more sequences at the same time, e.g. by aligning them and scanning them simultaneously. Similarly, the output device may output the results of the scanning steps for one or multiple sequences at the same time.

The output device may be of any suitable type, including but not limited to a printer, a display (e.g. a monitor that displays the results as a list, as a graph, or in some other suitable format), or a modem that sends out information (e.g. to another output device, to another computer, or to a storage device such as a DVD, CD, etc.).

Figure 13:
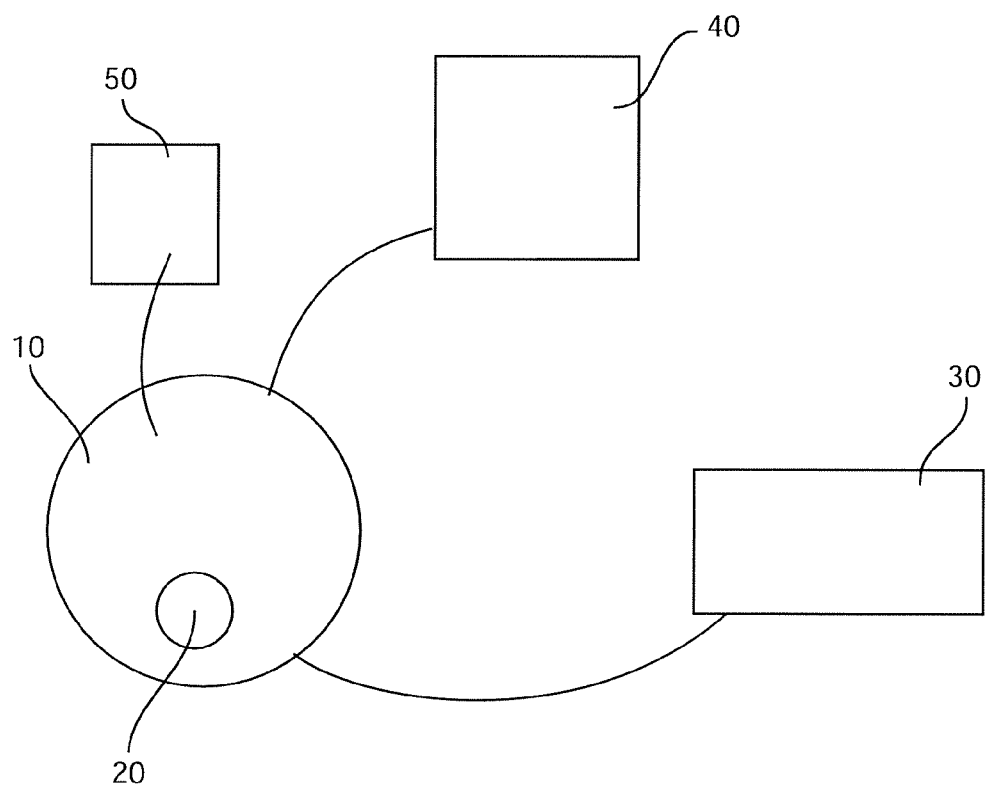
FIG. 13. Schematic representation of an exemplary computerized system of the invention.

Such a system is illustrated schematically in FIG. 13. FIG. 13 shows computer 10 with non-transient storage medium 20. Computer 10 is operationally linked to (or connected to, functionally connected to, or in electrical communication with) output device 30. In some embodiments, the computer is also operationally linked to nucleic acid sequencing apparatus 40, and data (e.g. a genomic nucleotide sequence, generally a DNA sequence) from nucleic acid sequencing apparatus 40 can be output and transferred to and received as input by computer 10 for analysis by the methods of the invention. In other embodiments, computer 10 is operationally linked to database 50 and information and/or data can be output from database 50 and transferred to and received as input by computer 10. Non-transient storage medium 20 contains computer executable instructions (e.g. code, computer program, etc.) which are performed by said computer and which cause said computer to carry out the steps of the methods described herein.

The following Examples are provided in order to illustrate exemplary embodiments of the invention but are not intended to limit the invention in any way.

EXAMPLES

Example 1

Epigenetic Transgenerational Inheritance of Vinclozolin Induced Mouse Adult Onset Disease and Associated Sperm Epigenome Biomarkers Abstract The endocrine disruptor vinclozolin has previously been shown to promote an epigenetic transgenerational inheritance of adult onset disease phenotype in the rat after fetal exposure during gonadal sex determination. This Example describes studies designed to investigate the transgenerational actions of vinclozolin on a second mammalian species (the mouse) and determine the alterations in the sperm epigenome. Transient exposure of the F0 generation gestating female during gonadal sex determination, embryonic days 7-13, promoted a transgenerational adult onset disease phenotype in the F1, F2 and F3 generation male and female mice. As the F3 generation mice reach one year of age they had an increase in spermatogenic cell defects, testicular abnormalities, prostate abnormalities and kidney abnormalities. Pathology analysis demonstrated 75% of the animals developed disease with 34% had two or more different disease states. Although full pathology analysis was not performed on females, a significant transgenerational increase in polycystic ovarian disease was observed. Analysis of the F3 generation sperm epigenome with a genome wide promoter analysis, MeDIP-Chip assay, identified differential DNA methylation regions (DMR) in 66 gene promoters and 40 of these DMR were confirmed and validated with a quantitative PCR analysis. These differential DNA methylation regions can potentially be utilized as epigenetic biomarkers for transgenerational exposure and disease.

Background

A factor to consider in disease etiology is the importance of early life exposures and events that are critical in later adult onset disease. These developmental origins of disease require a molecular mechanism that does not involve the induction of genetic abnormalities or alterations in DNA sequence. A molecular mechanism that has been shown to mediate the actions of environmental factors on disease is epigenetics.[1-3] Epigenetics is defined as molecular factors and processes around DNA that regulate genomic activity independent of DNA sequence, and that are mitotically stable.[1, 4] Epigenetic processes include DNA methylation, histone modifications, chromatin structure changes, and some small RNA's.[1, 5-10] The current study is focused on an investigation of how an environmental compound (endocrine disruptor) can promote the epigenetic transgenerational inheritance of adult onset disease states. DNA methylation is investigated since it is the primary epigenetic mechanism previously shown to mediate generational inheritance through the male germ line.[1, 11]

Endocrine disruptors are a class of chemical compounds readily available in the environment that are known to influence development and disease.[1, 2, 12-14] A number of studies have reported a correlation between endocrine disruptor actions and epigenetic changes.[11, 15-19] Previous studies have used the endocrine disruptor vinclozolin as a model environmental compound to investigate epigenetic transgenerational inheritance of disease. Epigenetic changes[11, 15] have been correlated with the incidence of transgenerational disease in rats after developmental exposure to the endocrine disruptor vinclozolin.[1, 2, 11, 15, 20] The process leading to epigenetic transgenerational changes involves a critical period during germ line epigenetic programming in which vinclozolin acts to permanently alter the germ-line (i.e. sperm) epigenome.[1, 11, 15] The subsequent generations (F1-F3) following the initial exposure develop a variety of transgenerational adult onset diseases in the rat.[1, 11, 20] This includes spermatogenic defects, testis abnormalities, prostate disease, kidney disease, immune abnormalities and female reproductive defects.[11, 20-23]

The current study was designed to extend these previous epigenetic transgenerational inheritance observations in the rat model[1, 11] using the mouse model. In addition, advanced epigenetic technologies[15] are used to identify epigenetic sperm biomarkers of transgenerational exposure and disease. The current study investigates the ability of the model endocrine disruptors vinclozolin and flutamide delivered to pregnant female inbred 129 mice and outbred CD-1 mice (i.e. F0 generation) prior to and during the period of sex determination (E7-E13) to promote transgenerational adult onset disease in subsequent generations (i.e. F1-F3). A genome wide promoter epigenome (DNA methylation) of the F3 generation sperm was mapped to identify differential methylation regions that can potentially be used as epigenetic biomarkers of exposure and adult onset disease.

In the current study, vinclozolin is used as a model endocrine disruptor with anti-androgenic activity. Vinclozolin ((RS)-3-(3,5-dichlorophenyl)-5-methyl-5-vinyl-1,3-oxazolidine-2,4-dione) is a systemic fungicide registered for use on fruits and vegetables and commonly used in the wine industry.[24] Rat embryonic exposure to vinclozolin promotes abnormal male sexual differentiation and development, as well as adult spermatogenesis.[11, 25, 26] Vinclozolin exposure of gestating female rats (F0 generation) prior to and during the period of gonadal sex determination, embryonic day 8-14 (E8-E14), has been shown to reduce the spermatogenic capacity of subsequent F1-F4 generation male rats,[11, 21] while exposure to vinclozolin later in gestation (e.g. E15-E20) had no effect on adult spermatogenesis.[25, 26] Flutamide is an androgen receptor antagonist previously used as a model anti-androgenic therapy[27-29] and shown to promote reproductive defects in rodents if administered prenatally.[30] In comparing the actions of vinclozolin and flutamide it was found that flutamide promoted an F1 and F2 generation phenotype, but not a transgenerational F3 generation phenotype, similar to that induced by vinclozolin.[27] Since the F1 and F2 generations can involve direct exposure, the F3 generation is the first generation not involving direct exposure.[31, 32] The F3 generation is used in the current study to assess epigenetic transgenerational inheritance in the mouse.

The transgenerational actions of vinclozolin appear to involve an epigenetic (i.e. DNA methylation) reprogramming of the male germ line.[11, 15] A recent independent study has demonstrated a transgenerational effect of vinclozolin on DNA methylation of several imprinted genes in a mouse model.[33] A study in an outbred strain of mice also showed that gestational exposure to parental oral vinclozolin produces a reduction in sperm count and sperm head abnormalities.[34] Other environmental factors shown to promote epigenetic transgenerational inheritance of disease or phenotypes include the plasticizer bisphenol A (BPA)[35] (Manikkam et al, submitted) and phthalates (Manikkam et al, submitted), dioxin[36] (Manikkam et al, submitted), pesticides[11] (Manikkam et al, submitted), hydrocarbons (Manikkam et al, submitted) and nutrition.[37-39] Therefore, a number of environmental factors can promote epigenetic transgenerational inheritance of adult onset disease. The current study was designed to investigate the potential epigenetic transgenerational actions of vinclozolin on adult onset disease in the mouse.

The critical period of exposure is fetal gonad sex determination[1, 2, 4] which involves testis determination that is initiated by the expression of the Sex determining Region of the Y chromosome (Sry) gene.[40] Gonadal sex determination and testis cord formation occurs between E12-E15 in the rat, while testis determination is initiated in the mouse embryo during E11-E12. The transgenerational phenotype induced in the rat[11] occurred when vinclozolin was administered at E8-E14 of gestation. Therefore, the treatment period of pregnant female mice (F0 generation) for the current study was adjusted earlier to E7-E13. During migration of the primordial germ cell down the genital ridge the germ cell genome (DNA) becomes demethylated upon colonization of the embryonic gonad.[1, 2] At the onset of gonadal sex determination the germ line then is re-methylated in a sex specific manner.[41] Therefore, the exposure of an environmental factor during this period has the ability to alter the germ line epigenome and if permanently modified can promote a transgenerational phenotype.[11, 15] Therefore, the basic molecular mechanism proposed for environmentally induced epigenetic transgenerational inheritance of adult onset disease involves: 1) environmental exposure during the gonadal sex determination period; 2) alteration in the epigenetic programming (DNA methylation) of the primordial germ cell; 3) permanent alteration in the male germ line epigenome with imprinted-like programming that escapes the de-methylation of DNA at fertilization and during early embryonic development; 4) transmission of the altered sperm epigenome (DNA methylation) to subsequent generations, similar to imprinted-like sites; 5) all cell types and tissues that develop from the sperm have an altered epigenome and transcriptome specific to the cell type or tissue; and 6) increased susceptibility to develop adult onset disease.

Results

Transgenerational Pathology Analysis

The experimental design involved exposing gestating female inbred 129 strain and outbred CD-1 strain mice to daily intraperitoneal (IP) injections of vehicle (DMSO) (control) or vinclozolin at two doses, 100 mg/kg/day (V1) or 200 mg/kg/day (V2), between embryonic day 7-13 of gestation. In addition, a comparison was used with flutamide IP injections at a 20/mg/kg/day dose. The F1 generation males and females from different litters were bred to generate the F2 generation animals and F2 generation males and females from different litters were bred to generate the F3 generation animals, see Methods below. No sibling or cousin breedings occurred to avoid any inbreeding artifacts. Selected F1, F2 and F3 generation animals from postnatal 90 (P90) or 300 (P300) days of age were analyzed for testis, sperm and other pathologies as previously described.[11, 20, 21]

The transient embryonic exposure to vinclozolin or flutamide in the mouse had no consistent transgenerational effects on litter size or male/female sex ratio in all generations analyzed. In addition, no consistent transgenerational differences were observed in body weight, testis weight index, or kidney weight index with either vinclozolin or flutamide exposure. Although selected generational effects were found, there was no consistent major vinclozolin or flutamide toxicity observed.

Figure 2B:
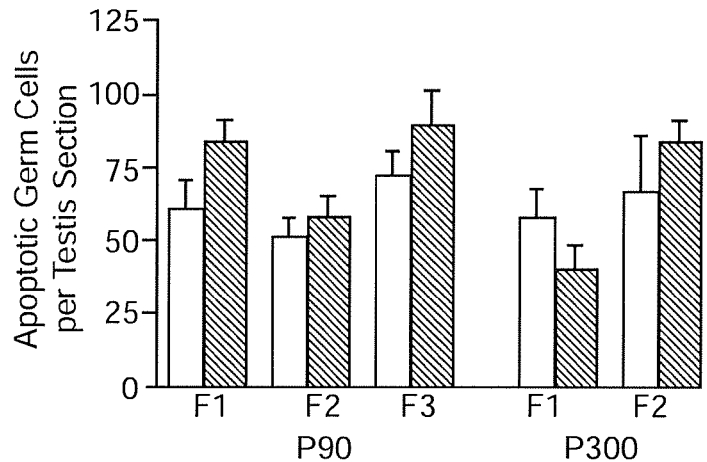
Figure 2C:
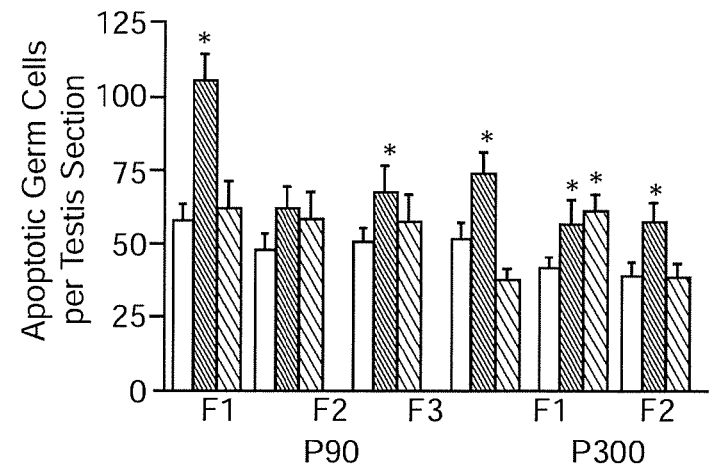
Figure 2D:
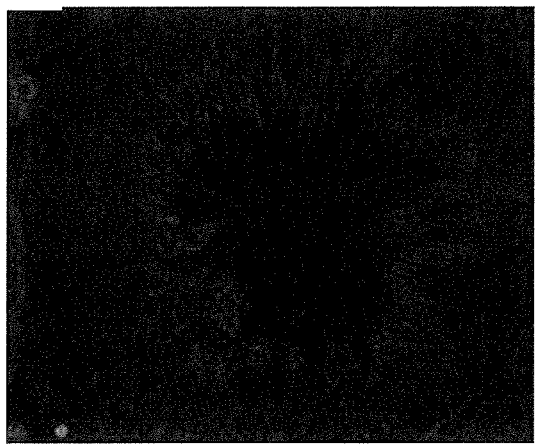
Figure 2E:
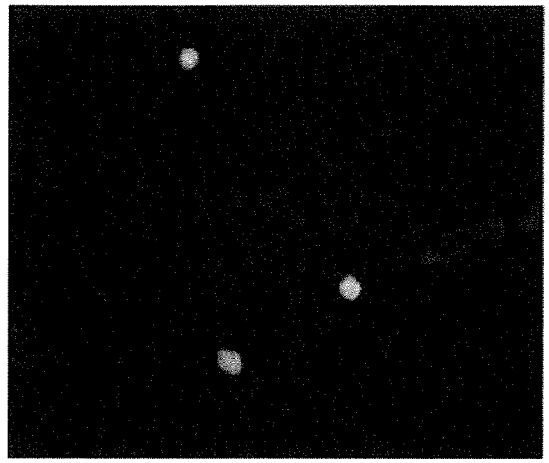

The mean number of apoptotic germ cells within the testes of male mice was increased in all the generations and ages analyzed (F1, F2, and F3 for P90, F1 and F2 for P300) of the 129 inbred strain vinclozolin group, FIG. 2A. There were no differences in apoptotic germ cells in the testis observed between control and flutamide 129 strain mice at any age or generation analyzed, FIG. 2B. The outbred mouse CD-1 strain V1 vinclozolin group showed significant increases in testicular apoptotic germ cells in the F1 and F3 P90 groups and F1, F2, and F3 P300 groups, FIG. 2C. Interestingly, the low vinclozolin V1 dose had a more consistent spermatogenic cell defect (i.e. apoptosis) than the higher V2 dose in the CD-1 strain. Therefore, vinclozolin induced a transgenerational (F1-F3) spermatogenic cell defect in both the inbred 129 strain and outbred CD-1 strain mice. Previous observations have demonstrated that spermatogenic cell apoptosis is a more sensitive physiological parameter than others in regards to epigenetic transgenerational inheritance phenotypes.[11, 20]

Transient exposure to vinclozolin and flutamide caused a reduction in the mean percentage of motile epididymal sperm primarily in the F1 generation males (not shown). A reduction in mean epididymal sperm concentration was also primarily observed in the F1 generation for vinclozolin and control samples. These reductions in mean sperm concentration were not observed in subsequent 129 mouse strain F2 or F3 generations. Although CD-1 strain vinclozolin mice showed reductions in mean epididymal sperm concentration for V1 mice in the F2 P90 group and V2 mice in the F3 P90 group, all other ages and generations analyzed showed no significant differences between control and treatment groups. Therefore, the transgenerational effects on sperm motility and number were not consistent with treatment or generation.

Figure 3A:
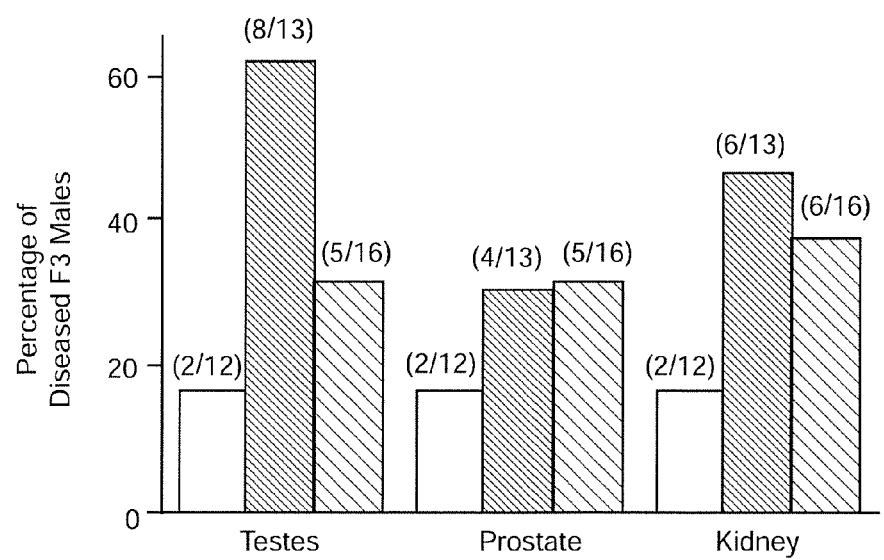
FIG. 3A-G. Disease frequency presented as (a) Percent of Disease F3 generation Males with the ratio of disease/total animal number presented above each bar for Control (open bar), V1 (black bar) and V2 (gray bar). Representative tissue micrographs from control (b,d,f) and V1 (c,e,g) F3 mice samples at P300 of age. (b) and (c) represent testis tubules cross sections at 100× magnification with 400× insets. (d) and (e) represent ventral prostate cross sections at 100× magnification with 400× insets. (f) and (g) represent kidney Bowman's capsule at 400× magnification.
Figure 3B:
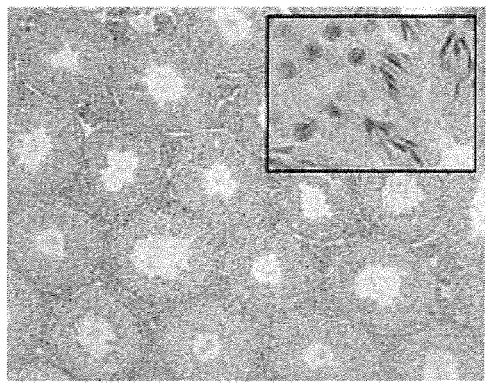
Figure 3C:
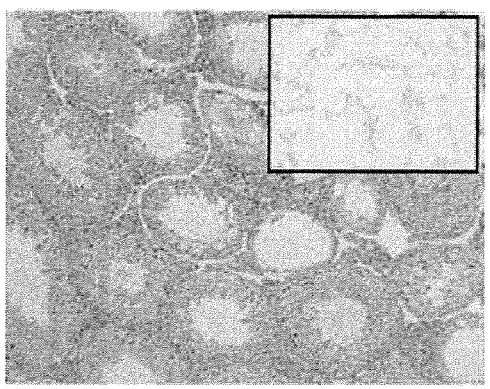
Figure 3D:
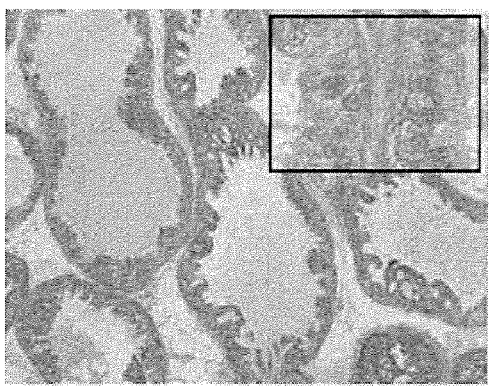
Figure 3E:
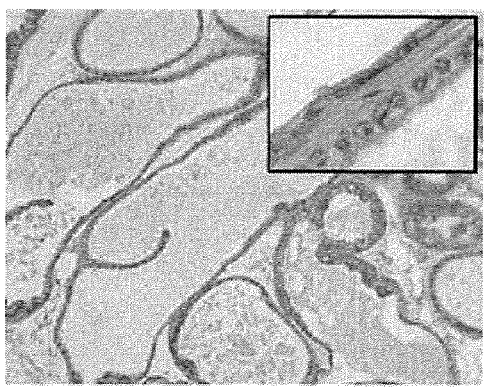
Figure 3F:
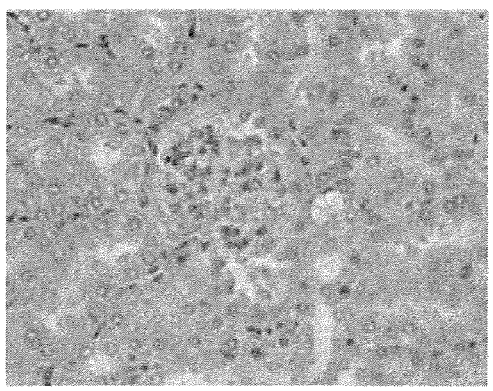
Figure 3G:
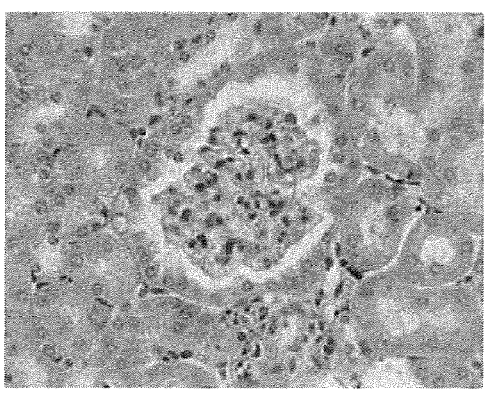

In the aged F3 generation CD-1 strain mice, there were increases observed in the proportion of vinclozolin lineage mice exhibiting abnormal disease-like characteristics in testis, prostate, and kidney tissues analyzed, FIG. 3A. The 1-year-old F3 vinclozolin generation CD-1 mice exhibited increased abnormalities in testicular tubules when compared to age-matched controls (FIGS. 3, B and C). In addition, vinclozolin F3 aged mice exhibited regression of prostatic secretory epithelium when compared to age-matched controls (FIGS. 3, D and E). The F3 P300 vinclozolin mice also had an increased percentage of cysts and thickened Bowman's capsules in the kidney (FIGS. 3, F and G). The number of P300 animals used is shown in FIG. 3A. A combination of all the disease-like states indicated 75% of the vinclozolin lineage F3 generation animals developed at least one disease and 34% had two or more disease states, which was significantly different from controls ($p<0.02$). In contrast to the CD-1 outbred mouse strain, the inbred 129 strain mice had no observable differences between treatment groups in adult onset disease of the prostate, kidney, testis or ovaries (data not shown). The control tissue histology shown in FIG. 3 was similar between the CD-1 and 129 strain mice. Therefore, the outbred strain appears more sensitive to vinclozolin induced transgenerational adult onset disease than the inbred strain of mouse.

Figure 4A:
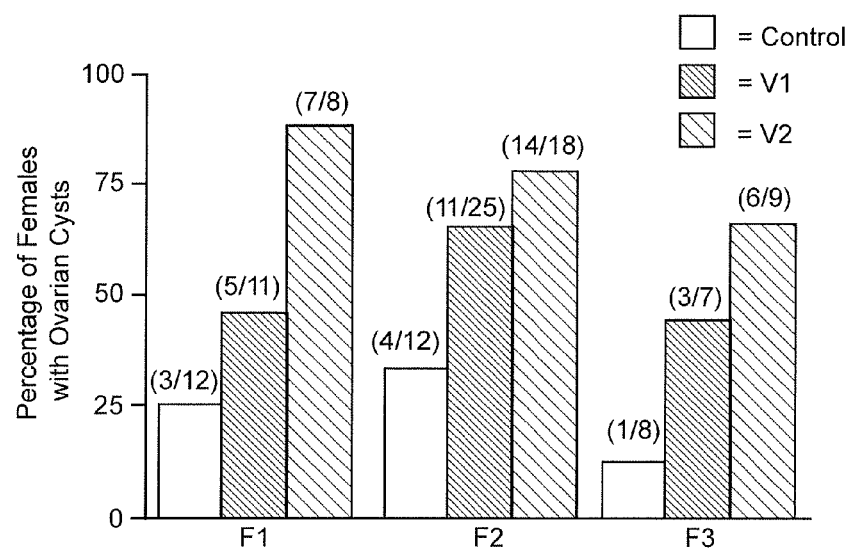
FIG. 4A-C. (a) Percentage of ovarian cysts in aged vinclozolin female CD-1 mice. White bar represents control, black bar represents V1, gray shaded bar represents V2. The ratio of animals with cystic ovaries/total animal number is presented above each bar. Representative histology of control (b) and vinclozolin (c) Representative ovaries are presented with arrow indicating an ovarian cyst.
Figure 4B:
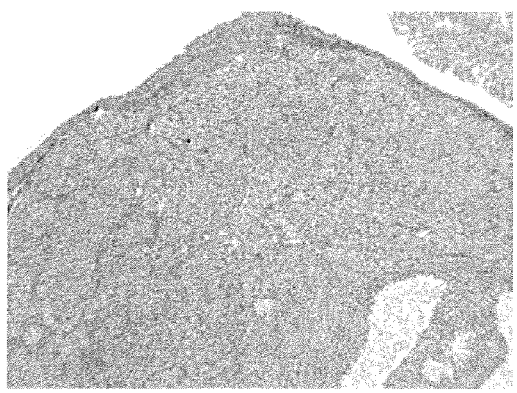
Figure 4C:

A thorough analysis of pathology in the females was not performed. However, one major abnormal phenotype was observed in the ovaries of vinclozolin F1-F3 generation animals. A significant increase in ovarian cysts was observed in all F1-F3 generations of V2 vinclozolin females ($p<0.05$), FIG. 4A. A larger number of ovarian cysts were observed in the V2 and V1 dose vinclozolin lineage females. The ovarian cysts are shown in FIG. 4C and demonstrate a lack of granulosa cells and oocytes with a predominant theca cell layer present. Therefore, vinclozolin also induced a transgenerational female ovarian cyst phenotype.

Transgenerational Effects on the Sperm Epigenome

Figure 5A:
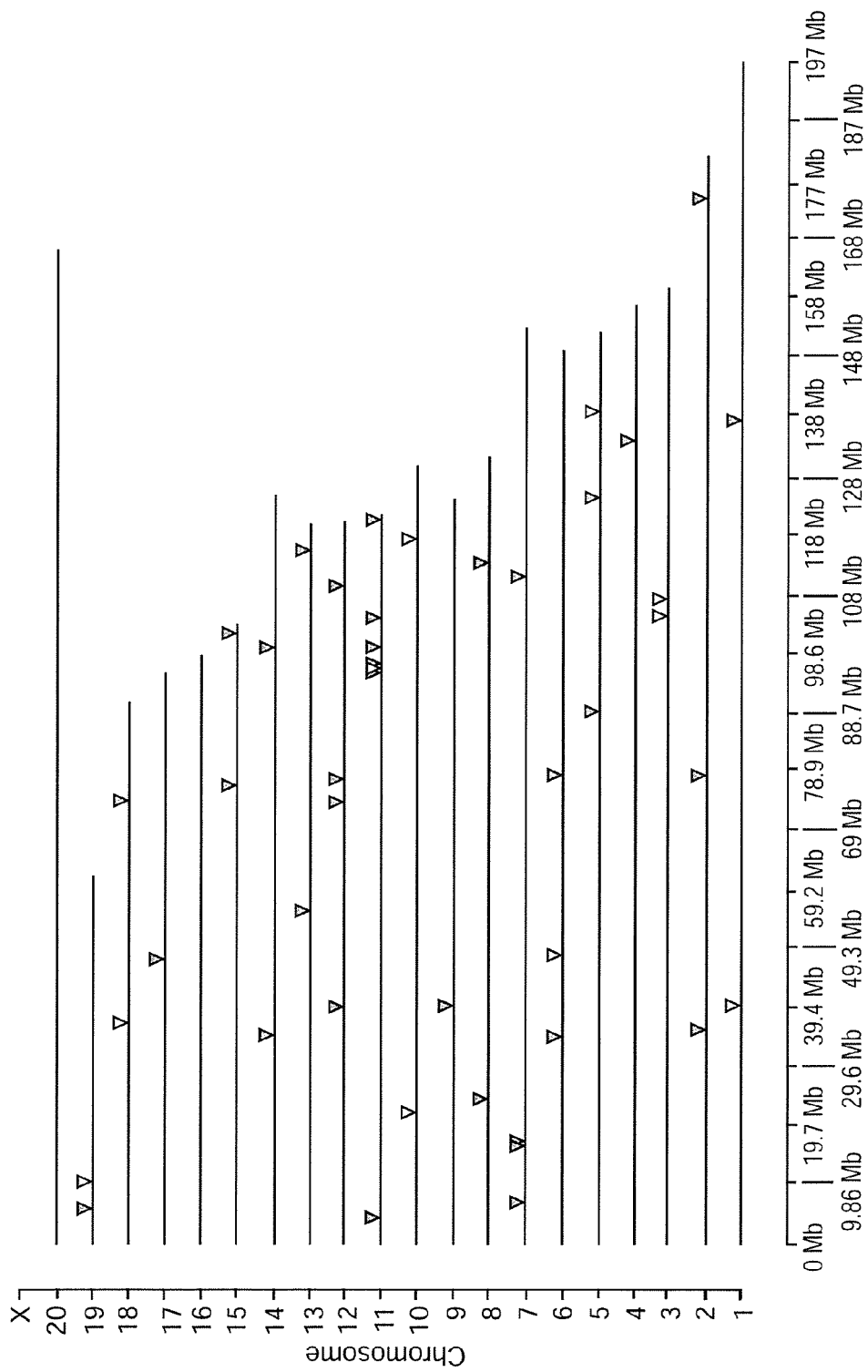
FIGS. 5A and B. Regions presenting vinclozolin-induced transgenerational change in F3 generation sperm DNA methylation: (a) chromosomal locations for regions detected with MeDip-Chip to have transgenerational change in DNA methylation for regions confirmed (closed arrowhead) and not able to be tested (open arrowhead) with Real Time qPCR validation are shown); (b) Real Time qPCR validation of regions showing transgenerational change in methylation with values presented as fold change of Vinclozolin/Control and normalized by DNA concentration in the MeDIP samples. The criteria for a RT-qPCR value to be considered as a change are a t-test with p<0.05, and the trend of the change observed in the qPCR is the same as the observed in the MeDIP-Chip array.
Figure 5B:
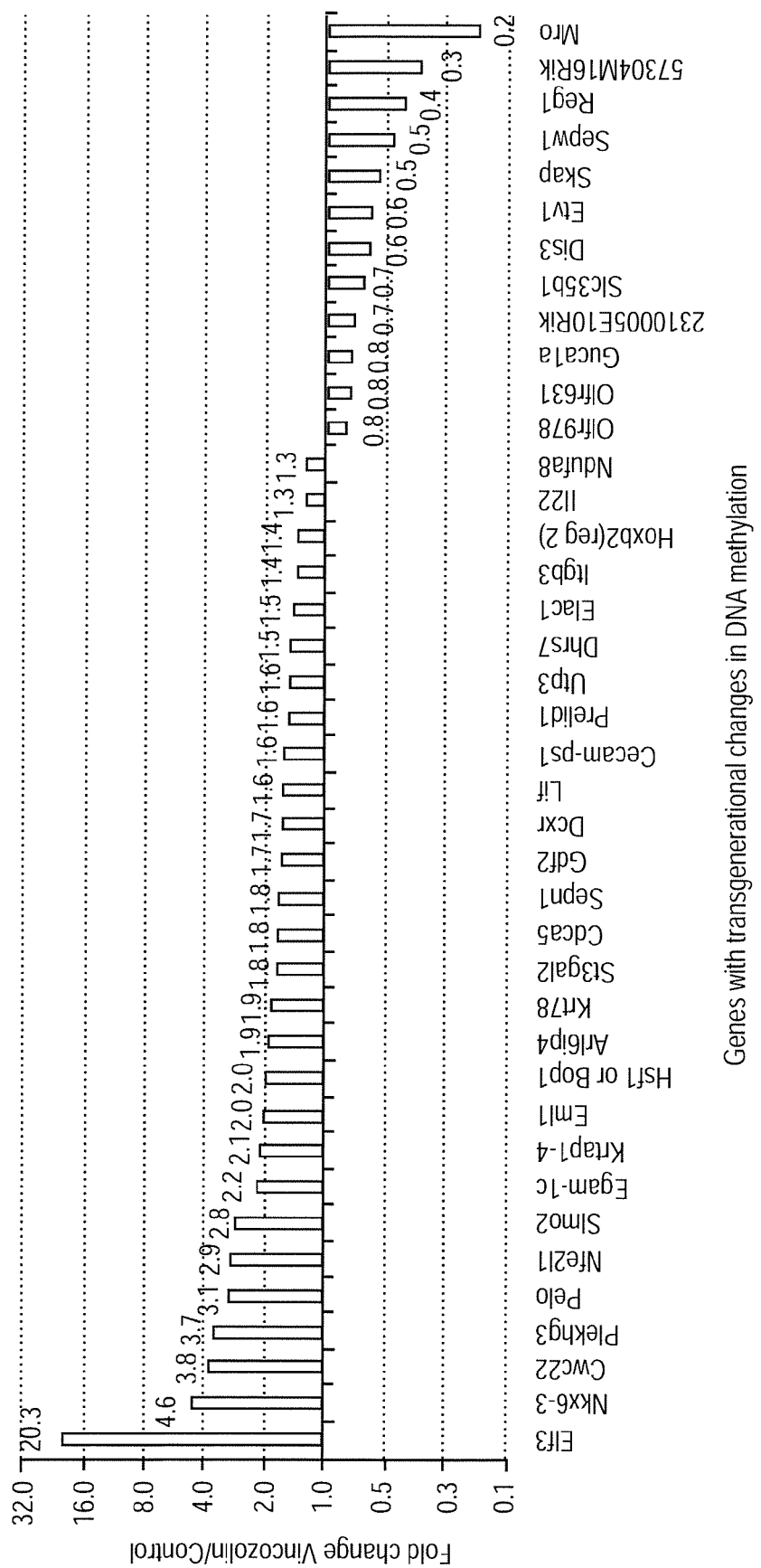
Figure 6A:
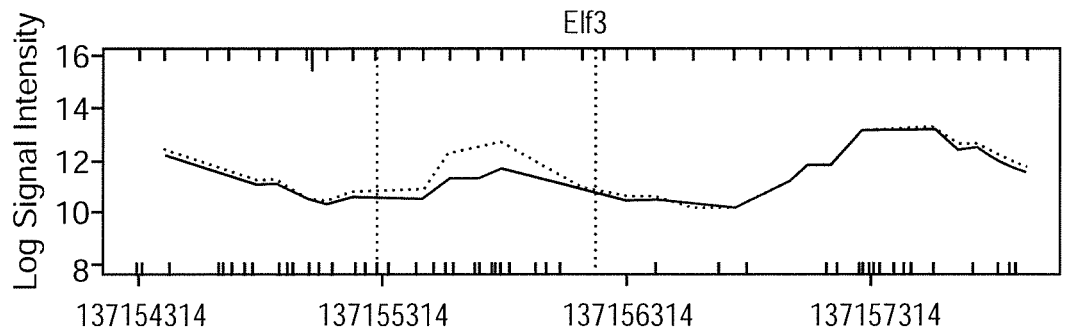
FIG. 6A-C. Examples of tiling array data for the most dramatic changes in DNA methylation (a) Elf3 or highest increase and (b) for Mro, for highest decrease. The log signal intensity for vinclozolin lineage, black line, and control lineage, gray line, is presented for chromosomal locations and the bar represents the site for qPCR confirmation. The distribution of differential methylation sites versus CpG density is shown in (c). Closed bar represent all regions significantly changed in the MeDIP-Chip array and hatched bar shows only confirmed regions by Real Time qPCR.
Figure 6B:
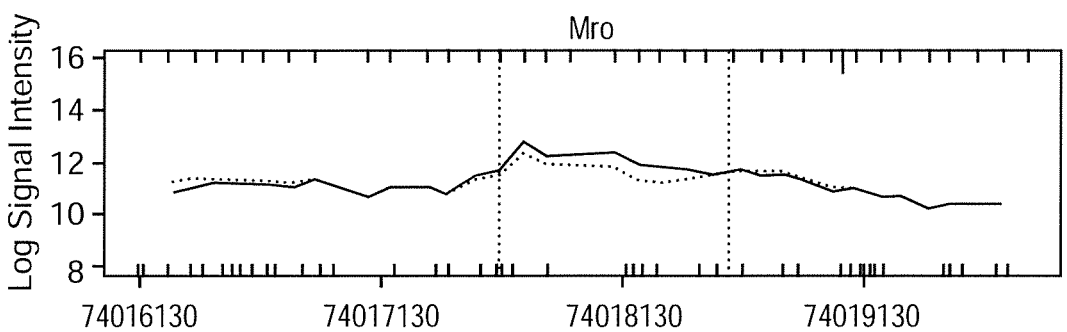
Figure 6C:
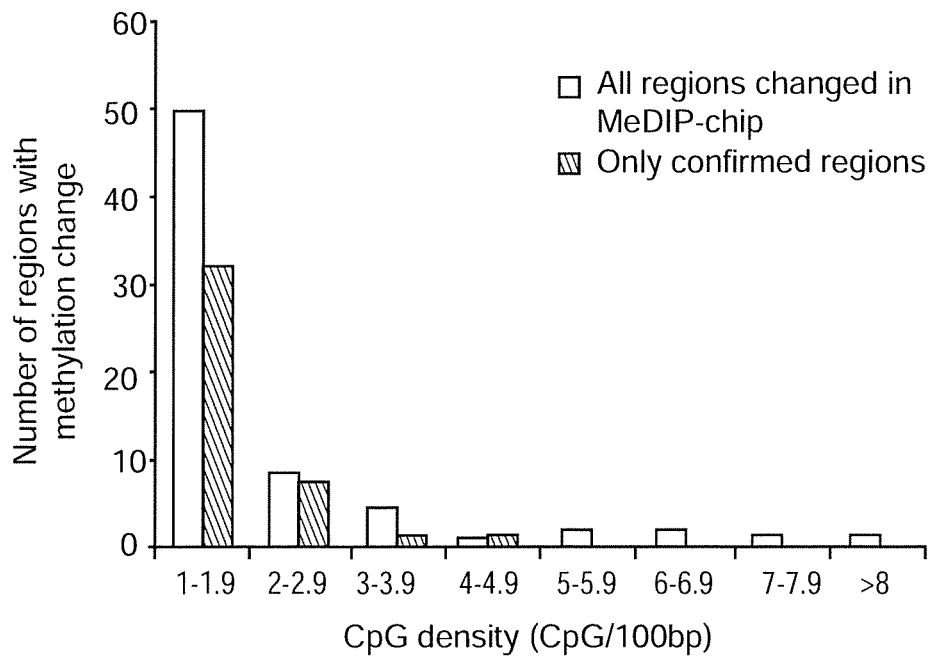

The transgenerational F3 control and vinclozolin generation sperm epigenomes were analyzed with a methyl cytosine antibody chromatin immunoprecipitation (MeDIP) followed by a genome wide promoter tiling array chip (MeDIP-Chip) assay.[15] The sperm DNA from F3 generation control and vinclozolin (100 mg/kg/day) lineage CD-1 outbred animals were analyzed. Two different experimental pools of control and vinclozolin lineage F3 generation MeDIP were generated, each containing sperm DNA from 3 different animals from different litters. A comparative hybridization with the MeDIP-Chip assay was performed as described in the Methods to identify differential DNA methylation between the control and vinclozolin sperm pools.[15] This analysis identified statistically significant differential DNA methylation regions (DMR) in 66 different promoters of average 800 bp in size. The results are shown in tabular form in FIG. 1A-C. The chromosomal locations of these differential methylation sites are presented in FIG. 5A as being increased or decreased in DNA methylation, FIG. 5B. Validation of MeDip-Chip results was performed through real time quantitative PCR[42, 43] with a minor modification. Real time qPCR quantification of each significant region obtained from the array was performed on the MeDIP samples and the values were normalized to the DNA concentration in the MeDIP samples. Ratios of vinclozolin/control from the quantitative PCR (qPCR) analysis on the MeDIP sperm DNA pools were used to confirm the changes observed in the tiling array and are presented in FIG. 5B. The combined tiling array data for each region that were confirmed or not able to be confirmed are shown in FIG. 5B. Some regions were not able to be confirmed due to technical limitations in the qPCR optimization. Approximately 25% of the sites were not confirmed with qPCR of the MeDIP samples. Two of these unconfirmed sites appeared to be hypervariable, indicating why they were not confirmed, but suggests they may be biologically important. The tiling array data for the sites with the largest increase (Elf3) and decrease (Mro) in methylation are shown in FIG. 6. Observations indicate 66 different promoters have transgenerational alterations in DNA methylation with the MeDIP-Chip and 40 were confirmed with qPCR. Previously 48 different promoters in rat sperm were identified with a comparative MeDIP-Chip analysis to have a transgenerational alteration in DNA methylation.[15] None of the gene promoters found in the mouse corresponded to the gene promoters identified in the rat sperm epigenome.[15] Therefore, as suggested from the imprinted gene literature, each species appears to have a unique transgenerational effect on the sperm epigenome.

Figures 1, 9:
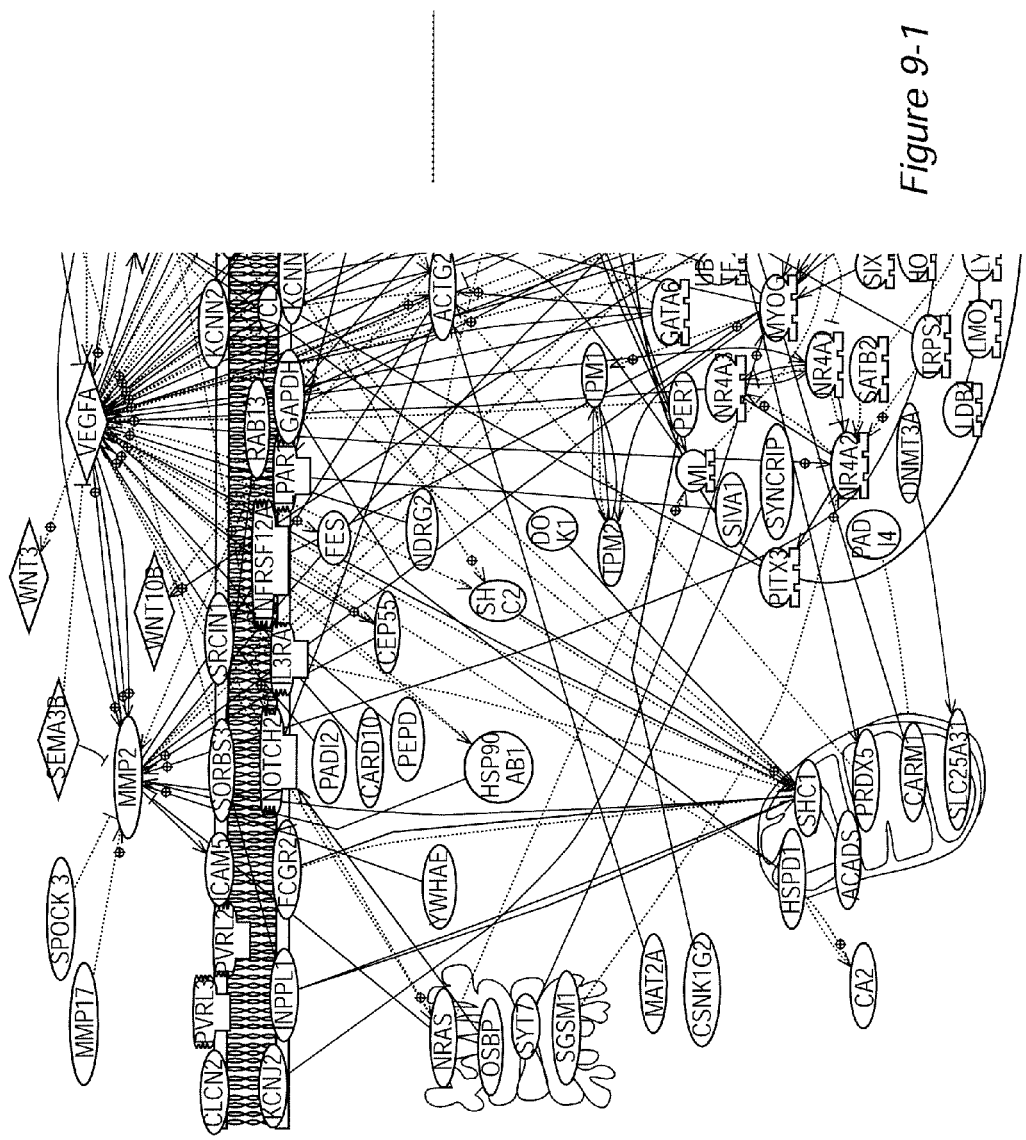
FIGS. 9-1 and 9-2. 9-1, representation of left portion and 9-2, representation of right portion of direct connection gene sub-network for combined genes with transgenerational DMR associated exposures for dioxin, Pesticide, Plastics or Hydrocarbons/Jet fuel indicated. Only 140 directly connected genes out of 499 unique genes associated with the combined lists are shown. Node shapes code: oval and circle—protein; diamond—ligand; circle/oval on tripod platform—transcription factor; ice cream cone—receptor; crescent—kinase or protein kinase; irregular polygon—phosphatase. Arrows with plus sign show positive regulation/activation, arrows with minus sign—negative regulation/inhibition; arrows represent regulation, expression, binding, promoter binding, and protein modification.
Figures 2, 9:
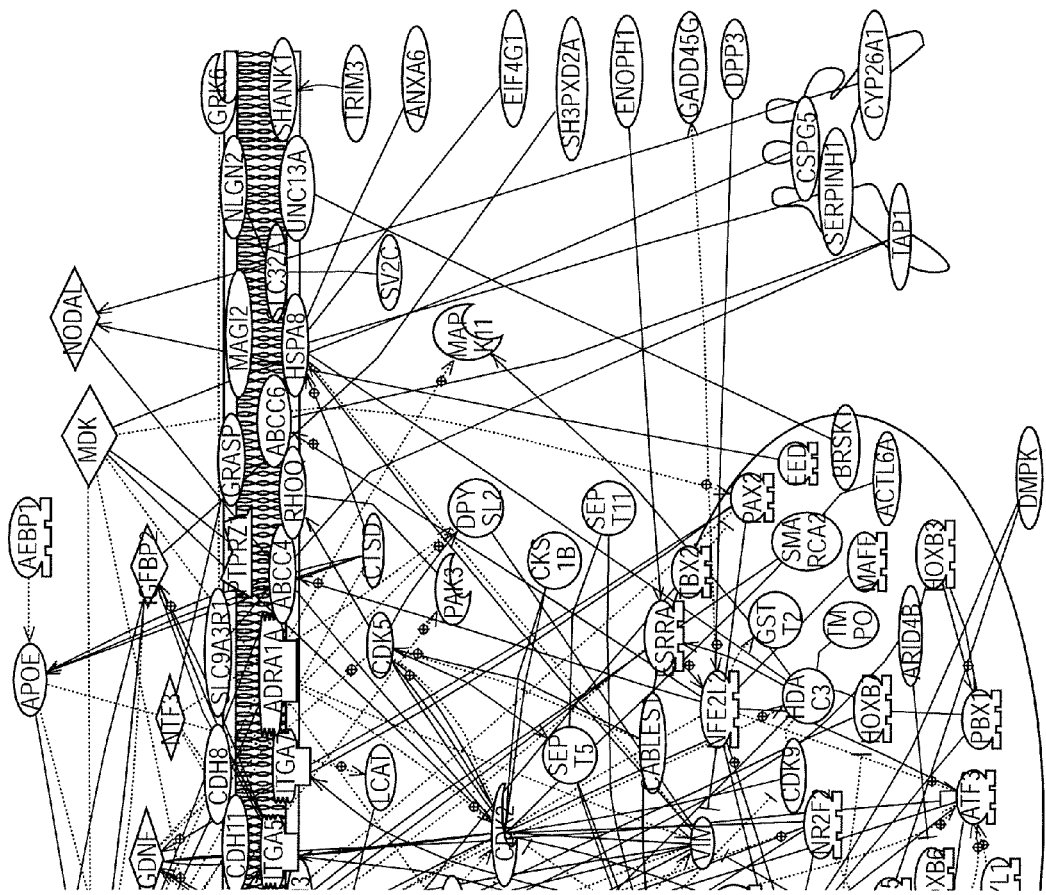

The MeDIP-Chip analysis presented in FIG. 1 and FIG. 5 involved the use of Nimblegen/Roche tiling arrays and a competitive hybridization of MeDIP samples (control versus vinclozolin) procedure.[15] An alternate procedure was used involving Affymetrix tiling arrays that require hybridization on two different chips and do not allow direct comparative hybridization. This procedure using duplicate arrays identified seven differential methylation regions, but none were confirmed using a bisulfite based PCR and mass spectrometry procedure.[15] Therefore, the MeDIP-Chip competitive hybridization approach used appears significantly more sensitive and accurate to identify differential methylation regions.

The previous analysis of transgenerational alterations in the rat sperm epigenome identified a consensus DNA sequence motif associated with a high percentage of promoter regions with transgenerational change in DNA methylation in the rat sperm.[15] This (Environmental Induced Differential Methylation Consensus Sequence Motif 1) EDM1 may provide a mechanism of why specific sites become permanently altered and associated with epigenetic transgenerational alterations in the sperm epigenome.[15] Analysis of the 40 confirmed vinclozolin-induced transgenerational DNA methylation changes in the mouse demonstrate the presence of EDM1 in 80% of the promoter regions and in only 16% of a set of computer generated random promoter sequences. The EDM1 motif was found in 83.3% of the total 66 regions identified. Observations suggest similar genomic features between species may exist at these regions. An additional genomic feature identified considered the CpG density of the differential DNA methylation regions. The largest number of DMR identified had a 1% CpG density with a subsequent decrease as the density increased to >8%, FIG. 6C. Observations indicate the low density CpG density of 1-8% is more sensitive to transgenerational alterations than the high-density sites (e.g. CpG islands). Therefore, a CpG cluster in a CpG desert may have an important regulatory role in environmentally induced epigenetic transgenerational inheritance. The MeDIP-Chip analysis used is not biased for CpG content, while next generation sequencing is biased to high density CpG and currently can not reliably analyze CpG<15-20% density. Therefore, the Me-DIP-Chip analysis was optimal for the current proposal.

Discussion

The current study was designed to investigate the transgenerational actions of vinclozolin on inbred and outbred strains of mice, and to identify epigenetic biomarkers in the sperm promoter epigenome. Gestating female mice during the developmental period of gonadal sex determination were transiently exposed to vinclozolin or flutamide to assess effects on transgenerational adult onset disease in the F1, F2 and F3 generations. The gestating females received daily intraperitoneal injections (IP) of pharmacologic doses of vinclozolin or flutamide. This study was designed to determine the potential to induce a transgenerational disease phenotype and investigate the molecular mechanisms involved, and was not designed to perform risk assessment or determine the potential environmental hazard of vinclozolin.

Analysis of litter size, sex ratio and body and tissue weights demonstrated no major toxicological effect of the vinclozolin or flutamide treatment on the F1 generation embryo exposed. Although some slight differences were observed with treatment and generations, no consistent effect was observed. These observations are important to exclude major toxicity effects as an initial mechanism for the transgenerational phenotypes observed. Similar observations were found with the rat model for both vinclozolin[11, 20, 21, 23] and flutamide.[27]

The transgenerational actions of vinclozolin on spermatogenic cells were observed in both the inbred 129 mouse strain and the outbred CD-1 mouse strain. The lower dose of vinclozolin had a more consistent action in the CD-1 mouse than the higher dose. The spermatogenic cell apoptosis was not observed after flutamide exposure for any generation examined. Previous studies have shown that flutamide can promote a spermatogenic cell defect in the F1 generation, but not the subsequent generations.[27] In this inbred 129 mouse strain flutamide had no effect on spermatogenic cell apoptosis. Therefore, the actions of vinclozolin are not simply due to anti-androgenic actions, as previously suggested[27], but instead potentially due to alternate signaling events and/or metabolites. Current observations demonstrate that vinclozolin promotes a transgenerational spermatogenic cell defect in both an inbred and outbred strain of mouse. In contrast to previous observations in the rat,[11, 21] no consistent effect was observed on sperm motility or numbers in the mouse.

Analysis of other adult onset disease-like conditions in the F3 generation male animals demonstrated abnormalities in the testis, prostate and kidney, FIG. 3. The testis abnormalities were associated with a loss of spermatogenic activity, reduction in germ cells per tubule cross section and increased number of tubules with no spermatogenic cells (azoospermia), as described in the Methods section. The prostate disease-like abnormalities are associated with prostate epithelial cell atrophy, periodic prostatitis and hyperplasia, as described in the Methods section. The kidney disease-like abnormalities are associated with an increase in cysts and increase in the thickness of the Bowman's capsule, as described in the Methods section. Previously, this kidney abnormality was shown to correlate with altered blood urea nitrogen (BUN) levels.[11, 20] The increase in disease frequency was similar for both doses of vinclozolin used. The induction of transgenerational onset disease by vinclozolin in this outbred CD-1 mouse is similar to the outbred Harlan Sprague Dawley rat previously described.[11, 20] The incidence of disease was higher in the rat model, but similar in phenotype. Therefore, vinclozolin promoted a transgenerational inheritance of adult onset disease in the outbred mouse model.

In contrast to the outbred CD-1 mouse strain, the inbred 129 mouse strain had no detectable transgenerational phenotypes in the testis, prostate or kidney. Although a spermatogenic cell apoptosis phenotype was observed in the 129 mouse strain after vinclozolin exposure, no other phenotypes were detected. Similar observations have been made in the rat model with an inbred Fisher strain[11] and inbred Charles River CD Sprague Dawley rat strain ([44] and data not shown). Therefore, spermatogenic cell defects may provide a more sensitive disease-like phenotype than the other abnormalities to monitor transgenerational phenotypes. This may be due to the role of the germ line in mediating transgenerational inheritance.[1] In contrast, the other disease phenotypes were not observed in the inbred strain of mouse suggesting inbreeding may reduce the frequency or ability to promote an epigenetic transgenerational inherited phenotype. Therefore, the inbred lines may have reduced responses to the epigenetic reprogramming of the germ line. Caution must be used in the design of transgenerational experiments using inbred lines of animals.[44, 45] The mechanism behind this inbred versus outbred line response remains to be elucidated and is anticipated to provide insights into the molecular basis of epigenetic transgenerational inheritance and phenomena such as hybrid vigor and inbreeding depression.

An interesting transgenerational phenotype observed after vinclozolin treatment of the outbred CD-1 mouse was a dramatic increase in cysts in the ovary. Polycystic ovarian disease is a common condition in the human population, but less common in species such as rodents.[46] This ovarian disease has dramatically increased in frequency in the human population (up to 18%) and has been shown to have a familial heritable association, but does not appear to follow normal Mendelian genetics.[47] The vinclozolin induced mouse polycystic ovary disease in the F3 generation females was more pronounced in the higher concentration vinclozolin exposure, FIG. 3. The morphology of the cysts are similar to those previously described as having no oocyte, limited granulosa cells and a thickened theca cell layer. Previous studies have suggested polycystic ovarian disease in humans may be an epigenetic disease.[47, 48] Although human polycystic ovarian disease is distinct and has endocrine and diabetes associated disease, the mouse disease observed has the same morphologic traits. The current study suggests environmental compounds such as vinclozolin could induce the disease state and that it may develop into a transgenerational phenotype for subsequent generations. Previously, a number of female transgenerational disease conditions were identified in the rat model[27], but were not investigated in the current mouse model study.

The mechanism behind the epigenetic transgenerational inheritance induced by environmental compounds like vinclozolin is an epigenetic reprogramming of the male germ line during gonadal sex determination.[1, 2] This epigenetic programming becomes permanent, similar to an imprinted-like DNA methylation site that is protected from demethylation at fertilization and early embryonic development, and the altered sperm epigenome is then transmitted to subsequent generations.[15] The ability of an environmental compound to act on the developing testis to modify the germ line epigenome is due to the primordial germ cell demethylation of DNA prior to gonadal sex determination and then remethylation during sex determination.[1, 49] A previous study of transgenerational alterations in the rat sperm epigenome identified 48 promoters that had differential DNA methylation using an MeDIP-Chip analysis.[15] Interestingly, a consensus EDM1 sequence motif was found to be present in 75% of promoters with confirmed transgenerational change in DNA methylation using the Glam2scan search tool.[15] The current study investigated the F3 generation outbred CD-1 mouse strain sperm promoter epigenome for differential DNA methylation sites. An MeDIP-Chip genome wide promoter analysis revealed 66 mouse promoters with differential DNA methylation regions. A quantitative PCR analysis of the MeDIP DNA samples confirmed the altered methylation in 40 sites. Two of the non-confirmed sites were found to be hypervariable in regards to data between samples. These hypervariable sites regions were present in the promoters of Gcgr and AK053193 genes and may be important regulatory sites as previously suggested.[2] A mixture of 28 increased and 12 decreased DNA methylation sites were observed. Interestingly, 80% of these promoters contained a previously identified differential methylation motif 1 (EDM1) site using the MCAST search tool.[15] However, none of the mouse differential methylation sites had any overlap with the rat differential methylation sites previously identified.[15] Past comparison of imprinted genes between species has demonstrated distinct species specific sites suggesting the epigenomes of different species will for the most part be distinct.[50] The epigenetic transgenerational sperm epigenome sites identified in the mouse and rat are distinct. Although some genomic features may be similar, such as EDM1 and lower density CpG region sensitivity, the actual sites for the sperm differential DNA methylation regions are not similar. The mouse differential methylation promoters identified vary from transcription regulators (Alx3, Hoxb3) to cytoskeleton and extracellular matrix problems (keratin 8, integrin beta 3).

The current study identified potential epigenetic biomarkers in the mouse sperm epigenome that identified animals that had an ancestral exposure to vinclozolin. In addition, these differential DNA methylation sites may act as biomarkers for the adult onset disease identified. The epigenetic transgenerational biomarkers are anticipated to be useful to potentially identify environmental exposures and provide early stage biomarkers for adult onset disease. This study confirms the ability of vinclozolin to promote an epigenetic transgenerational inheritance of adult onset disease in the mouse model. The identification of the alterations of DNA methylation in the F3 generation sperm suggests a role of epigenetic modifications in the germ line as mediating the transgenerational phenotype. The objectives of the current study were to replicate the vinclozolin induced epigenetic transgenerational inheritance of adult onset disease in a mouse model and document sperm epigenome alterations.

Epigenetic trans generational inheritance is thus an important alternate mechanism to the current paradigm of genetic elements being the primary contributors to disease etiology. The ability of environmental factors to alter epigenetics provides a unique mechanism for the environment to influence disease, independent of genetic abnormalities. A cooperative process involving both epigenetics and genetics may be important for some diseases.

Methods

The general experimental design involved the transient exposure of gestating 129 inbred and CD1 outbred mice (Charles River, Wilmington, Mass.) during the period of gonadal sex determination, embryonic day 7-13 (E7-E13). Daily intraperitoneal injection of vinclozolin or flutamide during the exposure period was used. The F1 generation offspring were bred to generate an F2 generation and then F2 generation bred to generate the F3 generation animals. No sibling or cousin breeding was used to avoid any inbreeding conflicts. Animals were sacrificed at postnatal day 90 (P90) and 300 (P300) for pathology analysis and sperm collection. The pathology of testis, prostate, kidney and ovary were assessed at P300 and sperm number and motility at P90. The sperm DNA was isolated to assess differential DNA methylation between control and vinclozolin lineage F3 generation samples. A methylated DNA immunoprecipitation (MeDIP) was performed and followed by a mouse promoter tiling array (Chip) using a comparative hybridization protocol.[15] The MeDIP-Chip differential DNA methylation sites identified were confirmed with a quantitative PCR analysis.

Animal Protocols and In Vivo Treatments

Timed pregnant inbred 129 mice were given intraperitoneal injections with vinclozolin (100 mg/kg·day, 99% pure; ChemService, West Chester, Pa.), flutamide (20 mg/kg·day, Sigma, St. Louis, Mo.) or DMSO in sesame oil (vehicle) as controls, while timed pregnant outbred CD-1 mice were given intraperitoneal injections (IP) with vinclozolin doses: 100 mg/kg·day (V1) or 200 mg/kg·day (V2) or DMSO in sesame oil as controls.[21] Mice were given injections from embryonic day (E) E7-E13, with plug date equal to day 0. Controls were injected with vehicle (DMSO) dose and were matched with vinclozolin or flutamide treatment animals within the same mouse strain at the time of injection and were analyzed together throughout all three generations. The number of treated gestating females used were: for mouse 129 strain (3 controls and 4 vinclozolin treated); for mouse 129 strain flutamide 20 mg/kg/day dose (3 controls and 3 flutamide treated); and for mouse CD-1 strain (4 control and 3 vinclozolin treated (100 mg/kg/day) (V1), 3 vinclozolin 200 mg/kg/day (V2)). F1 postnatal (P)P90 males and females from different litters of control, vinclozolin and flutamide treatment groups were bred to generate the F2 generation. F2 generation mice were bred to generate the F3 generation. Breedings were carefully monitored to eliminate any sibling or cousin breeding to remove potential phenotypes as a result of inbreeding. Male mice were collected and analyzed between P60-P90 (P90) for all generations and treatment groups. The number of P90 males collected for replicates for the mouse 129 strain vinclozolin treatment group (i.e. n value) were: for F1 (8 control, 11 vinclozolin); for F2 (11 control, 22 vinclozolin); and for F3 (11 control, 11 vinclozolin). The number of P90 males collected for replicates for the mouse 129 strain flutamide treatment group were: for F1 (8 control, 8 flutamide); for F2 (9 control, 8 flutamide); and for F3 (8 control, 8 flutamide). The number of P90 males collected for replicates for the mouse CD-1 strain vinclozolin treatment group were: for F1 (8 control, 6 V1, 8 V2); and for F2 (10 control, 10 V1, 6 V2). The numbers of P300 animals used are shown in FIG. 3A. All procedures were approved by the Washington State University Animal Care and Use Committee (IACUC approval #02568-024).

Sperm Motility and Concentration Analyses

The sperm motility was determined using caudal epididymal sperm. The epididymis was dissected free of connective tissue and a small cut made to the cauda. The tissue was placed in 2 ml F12 culture medium containing 0.1% BSA for 10 minutes at 37° C. Fifty microliters was placed on a warm slide and gently cover-slipped. The specimen was immediately examined using phase contrast microscopy with 200× magnification. The sperm motility assays examined rapid progressive, slow progressive and non-progressive motility according to WHO category.[51] The ratio of motile sperm to the total number of sperm, including immotile sperm, was calculated. Approximately 50-100 sperm were counted per microscopic field. The procedure was repeated at least twice with a new specimen from the same epididymis. Epididymal sperm count was determined using the same epididymis according to a previously described method with some modifications.[25, 52] Briefly, the epididymis that was placed in the 2 ml of culture medium was minced. The tissue pieces were stored at 4° C. for 48 hours to immobilize the sperm. Three independent sperm samples were counted using a hemocytometer. The counts were averaged and used as a replicate in statistical analysis. The control and vinclozolin generation analysis and the control and flutamide generation analysis for an individual experiment were done at the same time. All analyses were done blinded, such that different individuals were used for collection and counting.

Histology

The testes, epididymis, prostate and kidney were fixed in Bouin's fixative (Sigma) for 2 hrs, washed in 70% ethanol and embedded in paraffin using standard procedures. Three sections from each testis, epididymis, prostate and kidney were stained with hematoxylin and eosin using standard procedures for morphological analyses.

Pathology

Animal identification and treatment group were blinded to the researchers during analysis. Data were tabulated for each abnormality based on the percentage of tissue with pathological changes per total tissue per cross-section in two tissue cross-sections. Mice developing tumors were submitted as whole animals or excised formalin-fixed tissue for tumor identification. All tissue cross-sections were stained with hematoxylin and eosin for analyses. The testis cross-sections were determined to be abnormal if the number of tubules with atrophy, vacuoles or germ cell agenesis was greater than 20% of the total tubules present in the testis cross section.[21] Renal lesions were diagnosed by an increase in morphologically identified tubular damage.[20] The kidney was considered abnormal if more than 30% of the tissue contained tubular lesions. Kidney tubular changes involved extreme dilation with protein-rich fluids, fluid-filled cystic tubules, and thickening of the Bowman's capsule surrounding the glomerulus.[20] Ventral prostate tissue was considered abnormal if more than 30% of the prostatic ducts were atrophic and contained reduced columnar secretory epithelial cells.[22] Body and tissue (i.e. prostate, kidney, spleen, and testis) weights were monitored in age-matched adults.

Testicular Cell Apoptosis

The Fluorescein In Situ Cell Death Detection Kit (Roche Applied Science, Indianapolis Ind.) was utilized to detect apoptosis of testicular cells as described earlier.[25] The kit measures fragmented DNA from apoptotic cells by catalytically incorporating fluorescein-12-dUTP at the 3' DNA end using the enzyme terminal deoxynucleotidyl transferase (TdT), which forms a polymeric tail using the principle of the TdT-mediated dUTP Nick-End Labeling (TUNEL) assay. All the fluorescent cells in each testis section were counted at 400× magnification. The average number of fluorescent cells/whole testis cross section from one animal was used as a single value for statistical analysis. No significant change in tubule numbers per cross section was detected between the treatment lineages, so data was normalized per section.

Identification of Ovarian Cysts

Abnormalities in adult females of the F1, F2 and F3 generations were not extensively evaluated. However, at the time of sacrifice and dissection it was noticed that some females had cystic structures on their ovaries. These were grossly visible fluid-filled structures larger than normal Graffian follicles. If an animal had one or more cystic structures on one or both ovaries, then that female was considered to have cystic ovaries. A sub-set of 17 ovaries was also evaluated histologically, and there was concordance of ovaries labeled as cystic at gross dissection with the histologic presence of very large cystic structures. Cysts were defined as structures having a lining of none or a single layer of granulosa cells and an increased thickness of the surrounding stromal/thecal layer compared to what is found in large antral follicles.

Sperm Head Purification, DNA Isolation and MeDIP

Sperm heads were separated from tails and purified following the protocol described[53] (without protease inhibitors) from a total of six F3 vinclozolin generation mice and six F3 control generation mice in the range of 13-15 months of age. Sperm heads were then further purified using a 70% sucrose gradient centrifugation, based on the method described.[54] Purified sperm heads were resuspended in 1 ml buffer 0.5M tris-HCl, pH 8, 0.5M EDTA, 10% SDS and treated with 100 µl proteinase K (20 mg/mL) and 100 µl DDT (0.1 M) at 55° C. for 1 hour. DNA was precipitated with 50% isopropanol, washed with 70% ethanol and resuspended in DEPC $H_2O$. Individual sperm DNA was used as samples for further methylated DNA immunoprecipitation.[15] Two pools of samples were produced for each experimental treatment (control and vinclozolin), therefore each pool contained DNA from three animals from different litters. The MeDIP was performed as follows: 6 µg of genomic DNA was subjected to series of three 20 pulse sonications at 20% amplitude and the appropriate fragment size (200-1000 bp) was verified through 2% agarose gels; the sonicated genomic DNA was resuspended in 350 µl TE and denaturated for 10 min at 95° C. and then immediately placed on ice for 5 min; 100 µl of 5×IP buffer (50 mM Na-phosphate pH7, 700 mM NaCl, 0.25% Triton X-100) was added to the sonicated and denatured DNA.

An overnight incubation of the DNA was performed with 5 µg of antibody anti-5-methylcytidine monoclonal from Diagenode S.A at 4° C. on a rotating platform. Protein A/G beads from Santa Cruz were prewashed on PBS-BSA 0.1% and resuspended in 40 µl 1× IP buffer. Beads were then added to the DNA-antibody complex and incubated 2 h at 4° C. on a rotating platform. Beads bound to DNA-antibody complex were washed 3 times with 1 ml 1×IP buffer; washes included incubation for 5 min at 4° C. on a rotating platform and then centrifugation at 6000 rpm for 2 min. Beads-DNA-antibody complex were then resuspended in 250 µl digestion buffer (50 mM Tris HCl pH 8, 10 mM EDTA, 0.5% SDS) and 3.5 µl of proteinase K (20 mg/ml) was added to each sample and then incubated overnight at 55° C. on a rotating platform. DNA purification was performed first with phenol and then with chloroform: isoamyl alcohol. Two washes were then performed with 70% ethanol, 1 M NaCl and glycogen. MeDIP-selected DNA was then resuspended in 30 µl TE buffer. MeDIP sperm DNA was pooled into each of the four above mentioned groups, adding equal amounts of sperm DNA from each individual sample to the pools. Therefore, a total of four pools of MeDIP sperm DNA (C1, C2, V1 and V2) were used for the ChIP arrays.

Tiling Array MeDIP-Chip Analysis

Nimblegen Mouse Promoter 3×720K format microarray (Mouse Ref Seq promoter array) was used, each subarray contains 709,520 probes. These probes are of variable length from 50mers to 75mers. Each transcription start site tiled 2960 bps upstream and 740 bps downstream. The median probe spacing is 100 bps, the gap between the probe varying according to the exact length of the probe. There are 20,404 promoter regions for the Mouse array. A total of 1 microarray, 3 sub-arrays, were used, one each for V1 vs C1, V2 vs C2 and then the last one has a dye-swap of the first one C1 vs V 1.

Affymetrics' GeneChip® Mouse Promoter 1.0R Array was used, which contains 4.6 million probes tiled that interrogate nearly 28,000 mouse promoter regions. These probes are 25-mer and tiled at an average resolution of 35 bp with gaps of approximately 10 bp between probes. Each promoter region covers approximately 6 kb upstream through 2.5 kb downstream of 5' transcription start sites. A total of 6 arrays were used, one each for C1, C2, V1 and V2, one for C1+C2 and another for their DNA inputs, InpC1+InpC2.

Bioinformatic and Statistic Analyses of Chip Data

For each hybridization experiment, raw data from both the Cy3 and Cy5 channels were imported into R (R Development Core Team (2010), R: A language for statistical computing, R Foundation for Statistical Computing, Vienna, Austria. ISBN 3-900051-07-0,), checked for quality and converted to MA values (M=Cy5-Cy3; A=(Cy5+Cy3)/2). The following normalization procedure was conducted. Within each array, probes were separated into groups by GC content and each group was separately normalized, between Cy3 and Cy5 using the loess normalization procedure. This allowed for GC groups to receive a normalization curve specific to that group. After each array was normalized within array, the arrays were then normalized across arrays using the A-quantile normalization procedure.

Following normalization each probe within each array was subjected to a smoothing procedure, whereby the probe's normalized M values were replaced with the median value of all probe normalized M values across all arrays within a 600 bp window. If the number of probes present in the window was less than 3, no value was assigned to that probe. Each probe's A values were likewise smoothed using the same procedure. Following normalization and smoothing each probe's M value represents the median intensity difference between vinclozolin generation and control generation of a 600 bp window. Significance was assigned to probe differences between vinclozolin generation (V1 and V2) and control generation (C1 and C2) by calculating the median value of the intensity differences as compared to a normal distribution scaled to the experimental mean and standard deviation of the normalized M. A Z-score and P-value were computed for each probe from that distribution. Clustered Regions of interest were then determined by combining consecutive probes with significance p-values less than $10^{-7}$. The statistically significant differential DNA methylated regions were identified and P-value associated with each region presented. Each region of interest was then annotated for gene and CpG content. This list was further reduced to those regions with an average intensity value exceeding 9.5 (log scale), at least one 100 bp region with two CpGs or a CpG density>1%.

Quantitative PCR Methylation Analyses and Motif Search

The MeDIP-Chip differential DNA methylation sites identified were further tested with a quantitative PCR analysis.[42, 43] Real time qPCR quantification of each significant region obtained from the array was performed on MeDIP samples and the values were normalized to the DNA concentration of MeDIP samples measured by picogreen. These qPCR assays were optimized and performed by the Genomics Core Laboratory at the University of Arizona, Tucson, Ariz. For the motif analysis, the newly developed tool MCAST in MEME suite[55] was used to address the presence of the previously described EDM1 motif in mouse sequences.[15] EDM1 was tested with MCAST against the differential methylation regions and against a set of 150 R-code generated random promoters.

Statistical Analysis

For the litter size, weights and sperm analysis, data were analyzed with Student t-test in GraphPad Prism (GraphPad Prism Software, Inc., San Diego, Calif.). All values are expressed as the mean±SEM of the parameter measured, unless stated otherwise. Differences were considered significant at $p<0.05$. Statistical analyses were only done between control and vinclozolin or flutamide generation animals within each generation. Specific comparisons, analyses, and results are presented in the different figure legends. DNA methylation data were analyzed with Biostat 9.0 (Analystsoft). Paired T test was used for the comparisons and $p<0.05$ was considered for significant differences.

References for Background and Example 1

1. Skinner M K, Manikkam M, Guerrero-Bosagna C (2010) Epigenetic transgenerational actions of environmental factors in disease etiology. Trends Endocrinol Metab 21: 214-222.
2. Anway M D, Cupp A S, Uzumcu M, Skinner M K (2005) Epigenetic transgenerational actions of endocrine disruptors and male fertility. Science 308: 1466-1469.
3. Jirtle R L, Skinner M K (2007) Environmental epigenomics and disease susceptibility. Nat Rev Genet. 8: 253-262.
4. Kavlock R, Cummings A (2005) Mode of action: inhibition of androgen receptor function—vinclozolin-induced malformations in reproductive development. Crit. Rev Toxicol 35: 721-726.
5. Guerrero-Bosagna C, Settles M, Lucker B J, Skinner M K (2010) Epigenetic transgenerational actions of vinclozolin on promoter regions of the sperm epigenome. PLoS ONE 5: e13100.
6. Anway M D, Leathers C, Skinner M K (2006) Endocrine disruptor vinclozolin induced epigenetic transgenerational adult-onset disease. Endocrinology 147: 5515-5523.
7. Waterland R A (2009) Is epigenetics an important link between early life events and adult disease? Horm Res 71 Suppl 1: 13-16.
8. Bruner-Tran K L, Osteen K G (2011) Developmental exposure to TCDD reduces fertility and negatively affects pregnancy outcomes across multiple generations. Reprod Toxicol 31: 344-350.
9. Salian S, Doshi T, Vanage G (2009) Impairment in protein expression profile of testicular steroid receptor coregulators in male rat offspring perinatally exposed to Bisphenol A. Life Sci 85: 11-18.
10. Stouder C, Paoloni-Giacobino A (2010) Transgenerational effects of the endocrine disruptor vinclozolin on the methylation pattern of imprinted genes in the mouse sperm. Reproduction 139: 373-379.
11. Pimentel D, Cooperstein S, Randell H, Filiberto D, Sorrentino S, et al. (2007) Ecology of Increasing Diseases: Population Growth and Environmental Degradation. Human Ecology 35: 653-668.

12. Talsness C E, Andrade A J, Kuriyama S N, Taylor J A, vom Saal F S (2009) Components of plastic: experimental studies in animals and relevance for human health. Philos Trans R Soc Lond B Biol Sci 364: 2079-2096.
13. Bernal A J, Jirtle R L (2010) Epigenomic disruption: the effects of early developmental exposures. Birth Defects Res A Clin Mol Teratol 88: 938-944.
14. Hunt P A, Susiarjo M, Rubio C, Hassold T J (2009) The bisphenol A experience: a primer for the analysis of environmental effects on mammalian reproduction. Biol Reprod 81: 807-813.
15. Kitchen L W, Lawrence K L, Coleman R E (2009) The role of the United States military in the development of vector control products, including insect repellents, insecticides, and bed nets. J Vector Ecol 34: 50-61.
16. Birnbaum L S, Fenton S E (2003) Cancer and developmental exposure to endocrine disruptors. Environ Health Perspect 111: 389-394.
17. Baccarelli A, Bollati V (2009) Epigenetics and environmental chemicals. Curr Opin Pediatr 21: 243-251.
18. Ritchie G, Still K, Rossi J, 3rd, Bekkedal M, Bobb A, et al. (2003) Biological and health effects of exposure to kerosene-based jet fuels and performance additives. J Toxicol Environ Health B Crit. Rev 6: 357-451.
19. Wong S S, Vargas J, Thomas A, Fastje C, McLaughlin M, et al. (2008) In vivo comparison of epithelial responses for S-8 versus JP-8 jet fuels below permissible exposure limit. Toxicology 254: 106-111.
20. DiVall S A, Radovick S (2009) Endocrinology of female puberty. Curr Opin Endocrinol Diabetes Obes 16: 1-4.
21. Traggiai C, Stanhope R (2003) Disorders of pubertal development. Best Pract Res Clin Obstet Gynaecol 17: 41-56.
22. Rockett J C, Lynch C D, Buck G M (2004) Biomarkers for assessing reproductive development and health: Part 1—Pubertal development. Environ Health Perspect 112: 105-112.
23. Fisher J S (2004) Environmental anti-androgens and male reproductive health: focus on phthalates and testicular dysgenesis syndrome. Reproduction 127: 305-315.
24. Hauser R, Sokol R (2008) Science linking environmental contaminant exposures with fertility and reproductive health impacts in the adult male. Fertil Steril 89: e59-65.
25. Vujovic S (2009) Aetiology of premature ovarian failure. Menopause Int 15: 72-75.
26. Kumar S (2004) Occupational exposure associated with reproductive dysfunction. J Occup Health 46: 1-19.
27. Hotchkiss A K, Lambright C S, Ostby J S, Parks-Saldutti L, Vandenbergh J G, et al. (2007) Prenatal testosterone exposure permanently masculinizes anogenital distance, nipple development, and reproductive tract morphology in female Sprague-Dawley rats. Toxicol Sci 96: 335-345.
28. Watanabe N, Kurita M (2001) The masculinization of the fetus during pregnancy due to inhalation of diesel exhaust. Environ Health Perspect 109: 111-119.
29. Engelbregt M J, Houdijk M E, Popp-Snijders C, Delemarre-van de Waal H A (2000) The effects of intra-uterine growth retardation and postnatal undernutrition on onset of puberty in male and female rats. Pediatr Res 48: 803-807.
30. Anway M D, Rekow S S, Skinner M K (2008) Transgenerational epigenetic programming of the embryonic testis transcriptome. Genomics 91: 30-40.
31. Skinner M K (2005) Regulation of primordial follicle assembly and development. Hum Reprod Update 11: 461-471.
32. Brinkman A B, Simmer F, Ma K, Kaan A, Zhu J, et al. (2010) Whole-genome DNA methylation profiling using MethylCap-seq. Methods 52: 232-236.
33. Covert T, Guerrero-Bosagna C, Hague M M, Settles M, Anway M, et al. (2011) Epigenetic Biomarkers Associated with the Transgenerational Actions of the Endocrine Disruptor Vinclozolin on Mouse Adult Onset Disease. (Submitted).
34. Crews D, Gore A C, Hsu T S, Dangleben N L, Spinetta M, et al. (2007) Transgenerational epigenetic imprints on mate preference. Proc Natl Acad Sci USA 104: 5942-5946.
35. Nilsson E E, Anway M D, Stanfield J, Skinner M K (2008) Transgenerational epigenetic effects of the endocrine disruptor vinclozolin on pregnancies and female adult onset disease. Reproduction 135: 713-721.
36. Meredith S, Dudenhoeffer G, Jackson K (2000) Classification of small type B/C follicles as primordial follicles in mature rats. J Reprod Fertil 119: 43-48.
37. Tateno H, Kimura Y, Yanagimachi R (2000) Sonication per se is not as deleterious to sperm chromosomes as previously inferred. Biol Reprod 63: 341-346.
38. Ward W S, Kimura Y, Yanagimachi R (1999) An intact sperm nuclear matrix may be necessary for the mouse paternal genome to participate in embryonic development. Biol Reprod 60: 702-706.
39. Martinato F, Cesaroni M, Amati B, Guccione E (2008) Analysis of Myc-induced histone modifications on target chromatin. PLoS ONE 3: e3650.
40. Sadikovic B, Yoshimoto M, Al-Romaih K, Maire G, Zielenska M, et al. (2008) In vitro analysis of integrated global high-resolution DNA methylation profiling with genomic imbalance and gene expression in osteosarcoma. PLoS ONE 3: e2834.

Example 2

Transgenerational Actions of Environmental Compounds on Disease and Identification of Epigenetic Biomarkers of Ancestral Exposures Abstract Environmental factors during fetal development can induce a permanent epigenetic change in the germ line (sperm) that then transmits epigenetic transgenerational inheritance of adult onset disease in the absence of any subsequent exposure. The epigenetic transgenerational actions of various environmental compounds and relevant mixtures were investigated with the use of a pesticide mixture (permethrin and insect repellant DEET), a plastic mixture (bisphenol A and phthalates), dioxin (TCDD) and a hydrocarbon mixture (jet fuel, JP8). After transient exposure of F0 gestating female rats during the period of embryonic gonadal sex determination, the subsequent F1-F3 generations were obtained in the absence of any environmental exposure. The affects on the F1, F2 and F3 generations pubertal onset and gonadal function were assessed. The plastics, dioxin and jet fuel were found to promote early onset female puberty transgenerationally (F3 generation). Spermatogenic cell apoptosis was affected transgenerationally. Ovarian primordial follicle pool size was significantly decreased with all treatments transgenerationally. Differential DNA methylation of the F3 generation sperm promoter epigenome was examined. Differential DNA methylation regions (DMR) were identified in the sperm of all exposure lineage males and found to be consistent within a specific exposure lineage, but different between the different exposures. Several genomic features of the DMR, such as low density CpG content, were identified. Exposure specific epigenetic biomarkers were identified that may allow for the assessment of ancestral environmental exposures associated with adult onset disease.

Introduction

Epigenetic transgenerational inheritance provides an alternative molecular mechanism for germ line transmission of environmentally induced phenotypic change compared to that of classic genetics [1,2]. Most factors do not have the ability to modify DNA sequence, but environmental factors such as nutrition or various toxicants can influence epigenetic processes to mediate alterations in genome activity [1,3]. Environmental epigenetics focuses on how a cell or organism responds to environmental factors or insults to create altered phenotypes or disease. Previous observations have demonstrated that the exposure of a gestating female to the environmental fungicide compound vinclozolin [4] during fetal gonadal sex determination promotes a reprogramming of the male germ line epigenome [2]. The altered DNA methylation profile in the sperm becomes permanently reprogrammed to create an abnormal epigenome in the embryo and all cells and tissues derived from that embryo [5]. Later in life the animals develop adult onset disease states such as mammary tumors, prostate disease, kidney disease, testis abnormalities, and immune abnormalities at high (20-50%) frequencies [6]. Due to the imprinted-like nature of the altered epigenetic DNA methylation sites, the germ line (sperm) transmit this epigenome and adult onset disease phenotype to subsequent generations, which is termed epigenetic transgenerational inheritance [1]. The basic mechanism involves the ability of an environmental factor (compound) to alter the germ line DNA methylation program to promote imprinted-like sites that then transmit an altered epigenome and adult onset disease phenotype transgenerationally [1,2]. The vast majority of environmental exposures act on somatic cells at critical windows of development to influence phenotype and/or disease in the individual exposed, but this will not become transgenerational [1,3]. In the event the critical window for the primordial germ cell is affected by environmental exposure, the altered germ line has the ability to promote a transgenerational phenotype for subsequent generations [1]. More recently a number of reports have documented the ability of nutritional factors [7] and environmental toxicants such as bisphenol A (BPA), dioxin, vinclozolin and methoxychlor to promote epigenetic transgenerational inheritance [2,8,9,10].

The current study was designed to investigate the potential epigenetic transgenerational actions of a variety of different toxicants or mixtures of relevant compounds. This was initiated to determine the compound specificity to promote epigenetic transgenerational inheritance and to determine if the epigenetic alterations may provide biomarkers for exposure. The environmental compounds (toxicants) selected have been shown to have biological and health effects [11], and were identified as common suspected exposures of military personnel. In addition, the signal transduction for each exposure is unique. The first compound mixture is termed "plastics" and includes bisphenol A (BPA) and the phthalates DEHP and DBP which are the combined exposures from most plastics that have been shown to promote in vitro and in vivo toxicology [12]. Epigenetic effects of these compounds after neonatal exposures promotes adult onset disease [13,14]. The second mixture involves the most commonly used human pesticide (permethrin) and insect repellent (DEET), and is termed "pesticide" for this study, and has been shown to have negligible toxicology in either in vitro or in vivo studies [15]. The third compound used is dioxin (TCDD), which has been shown to have significant in vitro and in vivo effects in the promotion of cellular abnormalities and adult onset disease states [16]. Epigenetic parameters have been shown to be influenced by dioxin actions [17]. The fourth exposure is jet fuel (JP8) which is a "hydrocarbon" mixture that is a significant environmental exposure due to its use for dust control on road surfaces [18]. Toxicological effects have been shown in in vitro and in vivo studies with JP8 exposures [19]. The four exposures used are common environmental toxicants which have been generally shown to promote abnormal or disease phenotypes. The objective of this study was to determine the potential ability for these different compounds and mixtures to promote epigenetic transgenerational inheritance of disease and map the alterations in the sperm epigenome.

The potential transgenerational diseases investigated focused on pubertal onset parameters and gonadal functions associated with infertility. The incidence of altered pubertal onset has dramatically increased over the past several decades in human populations [20]. Pubertal onset can occur several years early in some women [21]. This early onset of female puberty has been shown to affect brain development, endocrine organ systems and growth, all of which potentially increase disease susceptibility later in life [22]. Although environmental exposures to endocrine disrupting compounds have been suggested as a causal factor [21], the basic mechanisms involved are unknown. The other disease parameters examined were associated with testis and ovary functions that influence fertility. In regards to testis function, sperm numbers and motility were examined, as well as spermatogenic cell apoptosis. In the human male population there has been a gradual decline in sperm number in most populations [23]. Estimates of male infertility appear to be over 10% in many human male populations [24]. In regards to ovarian function, the ovarian reserve or primordial follicle pool was assessed. An increasing percentage of the female population is developing premature ovarian failure associated with a loss of the follicle pool which promotes female infertility and affects approximately 15% of many female populations [25]. The causal factors for these gonadal disease phenotypes and increase in infertility are suggested to be due in part to environmental exposures to endocrine disruptor toxicants [26], but the basic molecular mechanisms involved are not known. The potential that the exposures used in the current study may promote the epigenetic transgenerational inheritance of these disease states is investigated.

Results

The current study was designed to investigate the potential ability of various environmental compounds and mixtures to promote epigenetic transgenerational disease with a focus on pubertal and gonadal abnormalities. The alterations in the sperm epigenome were investigated to determine the similarities and differences between the different exposures on differential DNA methylation. The experimental design used pharmacologic doses based on approximately1% of the lethal oral dose 50% (LD50) for most of the compounds that previously have been shown in vivo to not cause direct toxicological effects. Gestating female outbred Harlan Sprague Dawley rats were given intraperitoneal (IP) injections daily between embryonic days 8-14 of fetal development correlating with gonadal sex determination. No consistent effects were observed on litter size, sex ratios or weaning weights. The F0 generation gestating female was the only animal injected IP. The F1 generation animals at 90 days of age were mated to generate the F2 generation and the F2 generation were mated to generate the F3 generation progeny as previously described [2]. No sibling or cousin breedings were used to avoid any inbreeding artifacts. No major overt toxicological effects were observed in F1, F2 or F3 generations. The only treatment that promotes some toxicity in the F1 generation was the high dose plastics, so a lower dose at 50% was also used and termed "Low Dose Plastic" that had no toxicology. Anogenital distance was measured as an indicator of exposure to androgenic compounds that promote masculinization during the perinatal period [27,28]. Analysis of anogenital index (AGI) demonstrated some effects of the treatments on the F2 and F3 generation animals, but no effects at the F1 generation animals. These actions on the AGI in the F2 generation are possibly due to the direct exposure of fetal germ cells to the endocrine disruptor activities of several of the exposure compounds (e.g. BPA, DEHP, DBP) [12,13,14], while the increased AGI in the F3 generation could be transgenerational. The exposure of the F0 generation gestating female directly affects the F0 generation female, the F1 generation embryo and the germ line inside the F1 embryo that will be generating the F2 generation animal [1]. Therefore, phenotypes in the F0, F1 and F2 generations may be due to direct exposures and are not transgenerational effects or phenotypes by definition. A transgenerational phenotype or phenomena requires the lack of direct exposure to promote a generational effect [1,3]. The actions on F0, F1 and F2 are due to a direct multi-generational exposure and only the F3 generation phenotype can be considered a transgenerational effect.

Figure 7A:
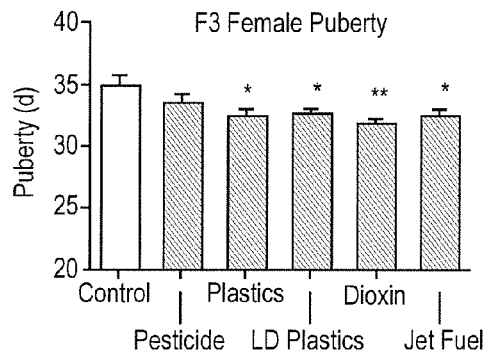
FIG. 7A-F. Ancestral (F0 generation female) exposures to environmental compounds promote transgenerational diseases, altering onset of puberty, testicular spermatogenic function and ovarian follicular development in F3 generation rat progeny. (A) Onset of female puberty was advanced from exposures to plastics, dioxin and jet fuel. (B) Onset of male puberty was unaffected from these exposures. (C) Increased apoptotic spermatogenic cells per testis section were observed from jet fuel exposure. (D) Total numbers of ovarian follicles per section were reduced in individuals from all exposures, (E) Total numbers of primordial follicles per section declined. (F) Total numbers of large ovarian antral follicles were unaffected. (*p<0.05; p<0.01, *p<0.001).
Figure 7B:
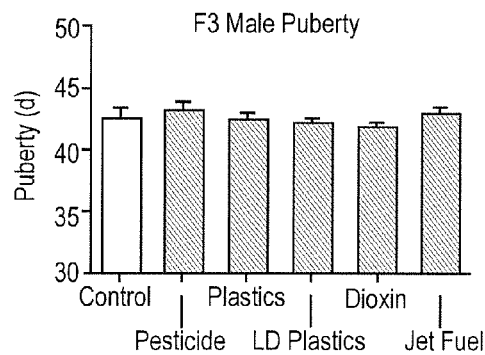

Puberty is a developmental process involving the hypothalamic—pituitary—gonadal axis which initiates during fetal development and matures in adolescence [20]. The onset of puberty was investigated with the different exposure lineages of control (DMSO vehicle), pesticide (permethrin and DEET), low and high dose plastics (BPA, DEHP and DBP), dioxin (TCDD), or hydrocarbons (jet fuel JP8) in the F1-F3 generation rats. The analysis was initiated for females at postnatal day 30 and males at postnatal day 35 until puberty (vaginal opening or balano-preputial separation) [29]. In the F1 generation plastics promoted delayed female pubertal onset, while in the F2 generation plastics, dioxin and jet fuel promoted early onset of puberty for females, with plastics and dioxin promoting early onset of puberty in males. In the transgenerational F3 generation it was demonstrated that plastics, low dose plastics, dioxin and jet fuel promotes early onset of puberty in females, while having no effect on males, FIG. 7A, 7B. Therefore, several of the exposures were found to promote early onset of puberty in females transgenerationally.

Figure 7C:
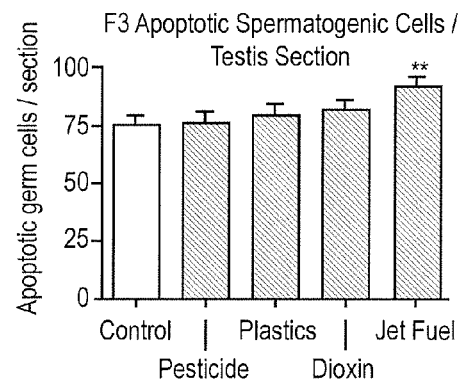
Figure 7D:
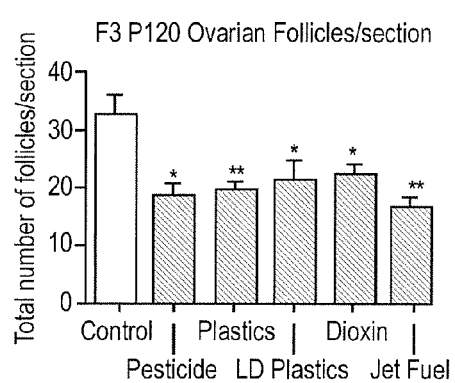
Figure 7E:
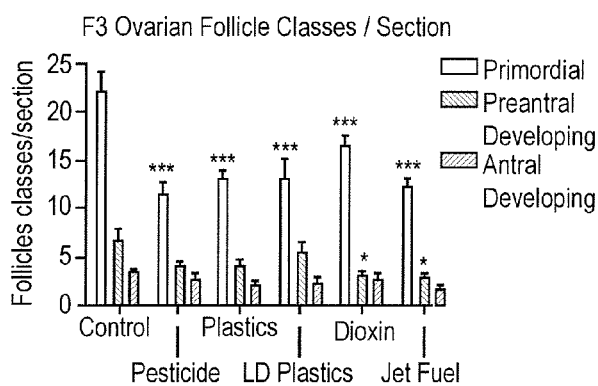
Figure 7F:
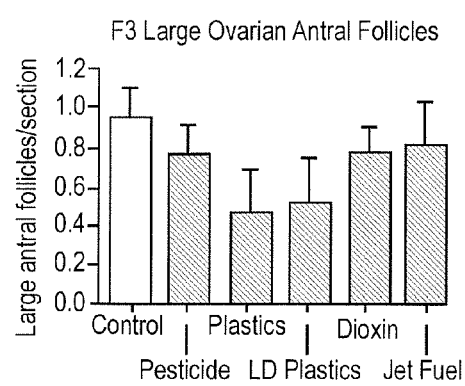

Gonadal function for both testis and ovary were investigated in the F3 generation at postnatal 120 days of age. Previously vinclozolin was shown to promote a transgenerational phenotype of spermatogenic cell apoptosis [2], so potential germ cell apoptosis in the testis was investigated. The jet fuel exposure was found to transgenerationally increase spermatogenetic cell apoptosis in the F3 generation male testis, FIG. 7C. Epididymal sperm concentration and motility for the F3 generation were also investigated and did not provide consistent alterations transgenerationally, as previously seen with vinclozolin exposure. The F3 generation ovaries were examined for total follicle number and the individual types of primordial follicles, primary follicles and developing follicles were categorized, FIGS. 7D and 7E. All the exposures were found to promote a transgenerational effect on the F3 generation ovary with a significant reduction in total follicle number, FIG. 7D, and the follicle class primarily affected was the primordial follicle, FIG. 7E. Therefore, all the exposures promoted the transgenerational phenotype of a reduction in the primordial follicle pool size. The large developing antral follicles were counted to determine potential effects on later stage follicle development and no differences were observed between the exposures when compared to control, FIG. 7F. The transgenerational action of the various exposures on the ovary was a reduction in the primordial follicle pool size. This may promote premature ovarian failure as the animals age. The testis and ovary are hormone regulated and both produce endocrine steroids. Hormone levels were analyzed to determine how the endocrine system was responding transgenerationally. The F3 generation males had a reduction in testosterone levels in the plastic, dioxin and jet fuel exposure lineages, while the females had no change in progesterone levels (not shown). No change in luteinizing hormone levels was detected in either male or female F3 generation animals. Therefore, the endocrine system was altered transgenerationally in the males.

Figure 8A:
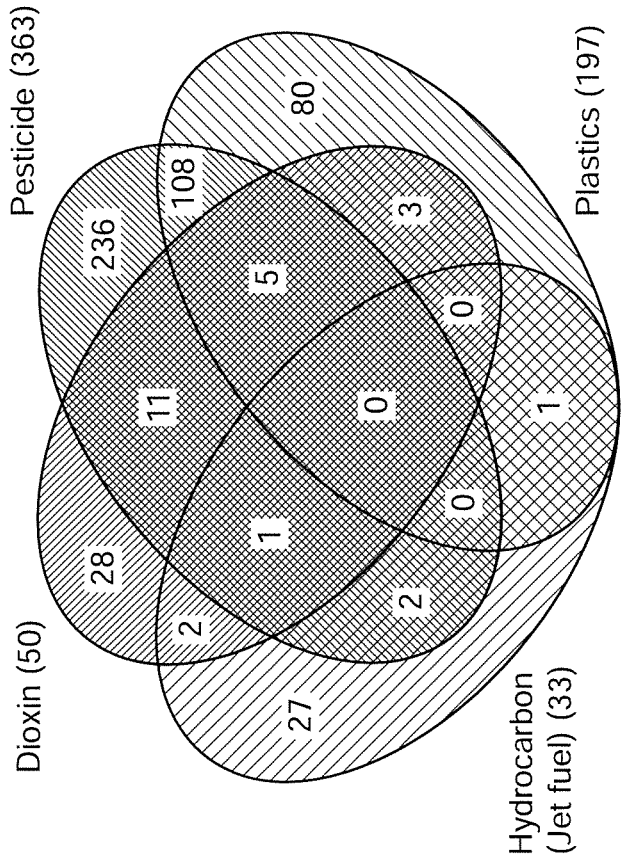
FIGS. 8A and B. The transgenerational DMR associated with each exposure group identified (total number). (A) Venn diagram of exposure DMR lists of F3 generation rat genes with differential DNA methylation due to in vivo exposure of F0-generation gestating female with dioxin, pesticide, plastics or hydrocarbons such as jet fuel. (B) Chromosomal location of DMR with arrows indicating values for plastics), dioxin, hydrocarbon and pesticide. The chromosome number and size are indicated. The box below the line indicates DMR cluster in 2-5 megabase regions with statistical significance (p<0.05).
Figure 8B:
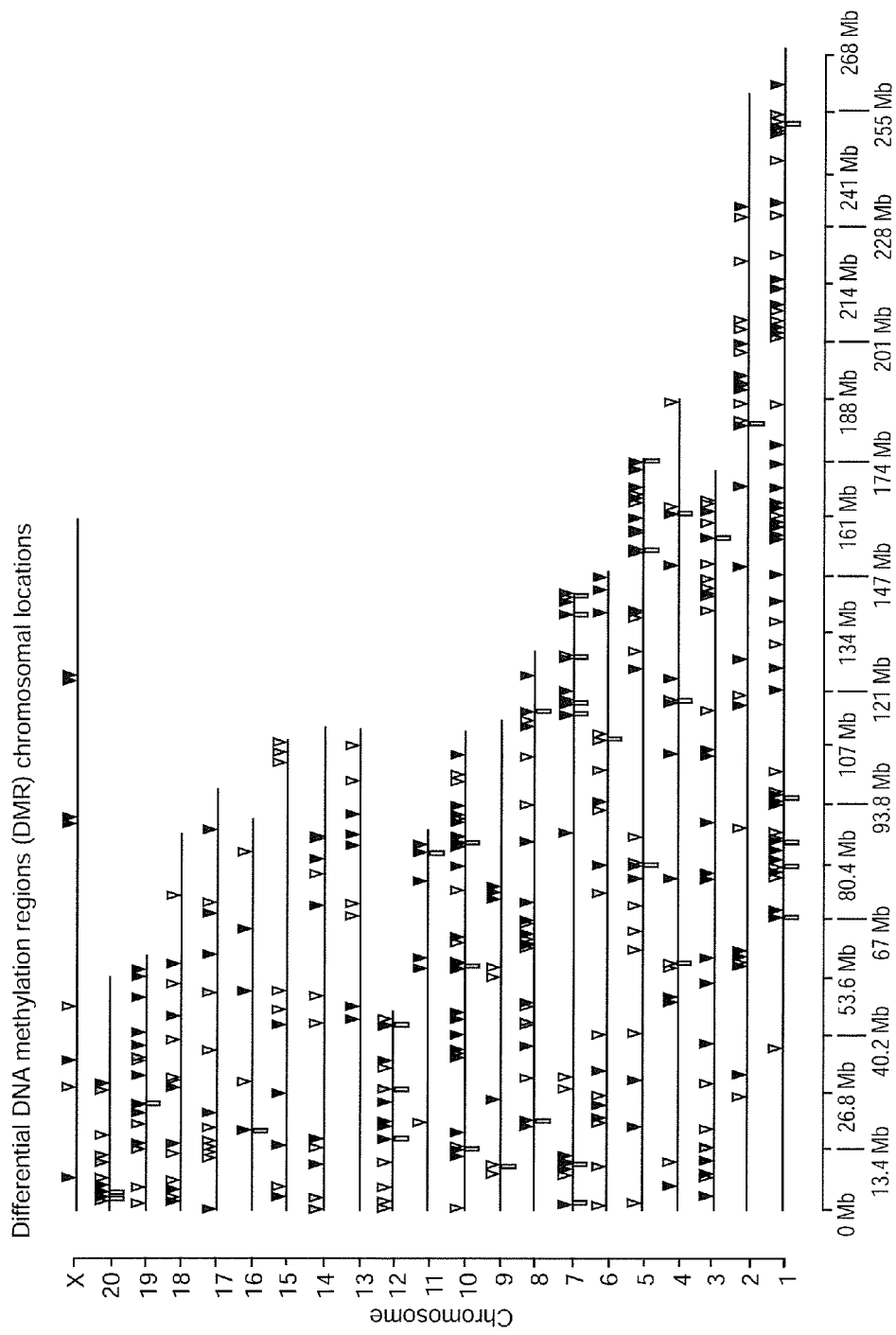

The mechanism involved in these transgenerational phenotypes is the reprogramming of the germ line (sperm) during male sex determination [1,3]. This altered sperm epigenome appears to be permanently reprogrammed and escapes the DNA methylation programming at fertilization to allow transgenerational transmission of the altered sperm epigenome, that then promotes all tissues developed from that sperm to have altered cell and tissue transcriptomes that can promote transgenerational disease [1]. Previously, vinclozolin was shown to promote a transgenerational (F3 generation) alteration in DNA methylation [2,5] and a transgenerational transcriptome alteration in tissues like the testis [30]. The F3 generation rat sperm from the control and all exposure groups were collected for genome wide promoter DNA methylation analysis [5]. The procedure involved the use of an antibody to methylcytosine to immunoprecipitate methylated DNA (MeDIP) and then a competitive hybridization tiling array (Chip) for a MeDIP-Chip analysis [5]. Differentially methylated sites were identified for all the different exposure lineages in the F3 generation sperm when compared with vehicle control F3 generation sperm. The overlap of the DMR sets for each exposure is shown in a Venn diagram in FIG. 8A. The number of DMR for hydrocarbons (jet fuel) was 33, dioxin 50, plastics (BPA, DEHP, DBP) 197 and pesticide (permethrin and DEET) 363 with a statistically significant difference ($p<10^{-5}$). Interestingly, the majority of each DMR set was specific to an exposure group and not common with the other exposure DMR's. The only exception was an overlap between plastics and pesticide of 113 DMR's, FIG. 8A. Therefore, each exposure had a unique signature of epigenetic alterations in the F3 generation sperm. The chromosomal localizations of these sites are shown in FIG. 8B. The DMR's are seen on all autosomes and the X chromosome. Clustering analysis of the DMR's when over represented in specific chromosomal locations identified 35 different clusters (2-5 megabase each) of DMR between the exposures that with z-score analysis have a statistically significant difference ($p<0.05$), FIG. 8B. These DMR clusters may represent "epigenetic control regions" where different exposure DMR's may commonly regulate genome activity. In considering the combined DMR and associated gene promoters for all exposures, the potential cellular signaling processes affected demonstrated similar pathways are predominant. A gene network analysis for direct connections within the total gene set associated with the DMR is shown in FIG. 9 and demonstrates extracellular, membrane, cytoplasmic and nuclear associated genes are all associated with the DMR identified. Common cellular signaling pathways and processes appear to be involved from the gene network identified. Therefore, common cellular pathways and gene networks may be influenced by the different exposures and transgenerational sperm epigenomes. Although exposure specific transgenerational differential DNA methylation regions (DMR) are predominant, the common cellular processes and gene networks affected may explain the similar disease phenotypes observed.

Figure 10B:
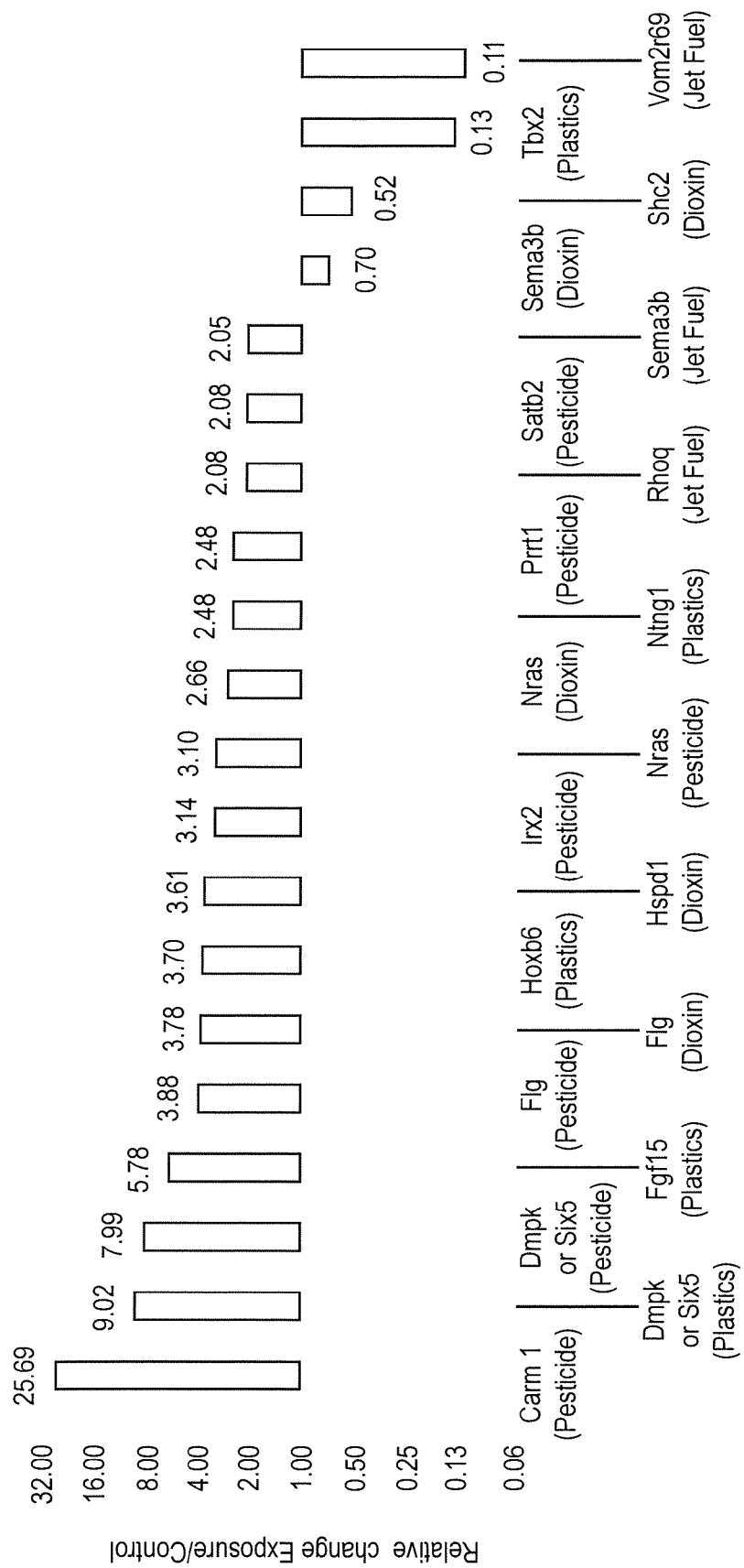
FIGS. 10A and B. The MeDIP-qPCR analysis of (A) selected DMR for each exposure was used to confirm MeDIP-Chip analysis and (B) relative change (exposure/control) ratio presented for each DMR. All changes shown are statistically significant between control and exposure (p<0.05).
Figure 11:
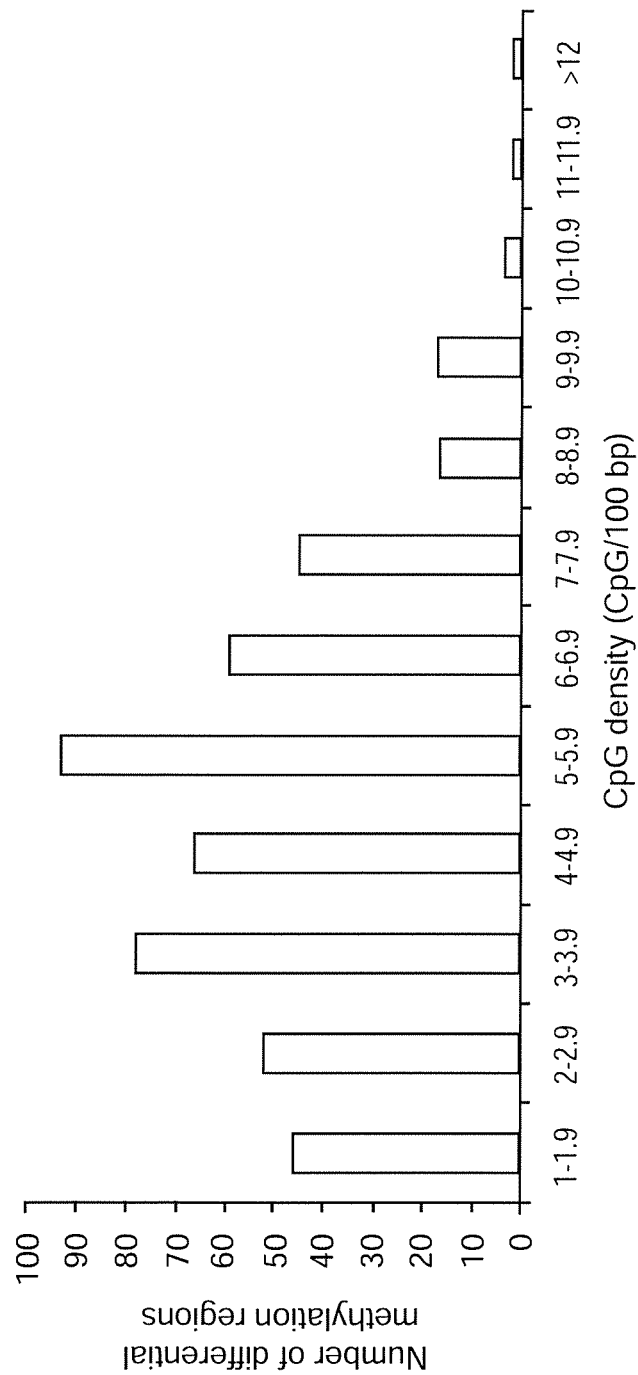
FIG. 11. Differential DNA methylated region (DMR) CPG density. The CpG density (CpG/100 bp) associated with all exposure DMR are presented with number of DMR versus density (CpG per 100 bp).

The identification of epigenetic alterations in specific regions of the F3 generation sperm support a role for epigenetic transgenerational inheritance of the disease phenotypes observed. Several of the top exposure specific DMR's for each exposure with the highest statistical significance were selected for confirmation with quantitative PCR of the MeDIP samples. A list of the confirmed exposure specific signatures is presented in FIG. 10. In addition, several of the top overlapped (common) DMR were also selected and shown. The MeDIP qPCR analysis demonstrated both increases and decreases for the exposure specific and common DMR, FIG. 10B. These exposure specific DMR are considered potential epigenetic biomarkers for exposure and the transmission of transgenerational phenotypes. Further analysis of the epigenetic sites identified considered two genomic features associated with the DMR's. The first one was a DNA sequence motif termed "Environmentally Induced DNA Methylation Region 1" (EDM1) that was previously identified and shown to be associated with a high percentage of the vinclozolin induced sperm DMR's [5]. This motif may not be at the specific altered DNA methylation site, but is within the 400-500 bp region. A DNA sequence motif such as EDM1 may promote a region of sensitivity for these DMR's to be programmed transgenerationally. The potential presence of this EDM1 motif in the epigenetic sites (DMR) identified in the current study for all the exposures was determined. An evaluation of the presence of EDM1 using the MCAST online software revealed a statistically significant higher EDM1 presence in promoter regions of the JP8 and dioxin exposure groups (74.19% and 57.63%, respectively) compared to a computer generated random set of 144 promoters (20.83%). The presence of EDM1 in the promoter regions of the plastics (20.47%) and pesticides (7.36%) was similar or below its presence in the random set of promoters. This suggests that the molecular mechanisms involved in the targeting of these regions to produce a transgenerational change in DNA methylation may differ among the exposure groups. Another genomic feature investigated was the CpG density within the DMR identified. The frequency of CpG number per 100 bp for the DMR demonstrates the DMR identified for all exposures have a CpG content of between 1-8 CpG/100 bp with none above 15 CpG/100 bp, FIG. 11. A small CpG cluster in a CpG desert appears to be a primary feature of the transgenerational DMR identified, and not shores or islands of CpG. Therefore, specific genomic features such as low CpG density, isolated CpG clusters, and the presence of a unique DNA sequence motif may be involved in facilitating the programming of these epigenetic sites (DMR) in the male germ line.

Discussion

The current study used pharmacologic doses of all the compounds and mixtures based on approximately 1% of the oral LD50 dose for most exposures (compounds. The objective was to determine if these exposures have the capacity to promote epigenetic transgenerational inheritance of a disease phenotype, and not to do risk assessment of the exposures. Now that the current study has established the transgenerational actions of these compounds, risk assessment toxicology involving dose curves of relevant environmental doses are needed. In addition to considering the mode of administration and dose, the critical window of exposure to promote the epigenetic transgenerational phenotype is gonadal sex determination, which for the human is 6-18 weeks of gestation. The gestating women in the first half of pregnancy would be the population most sensitive to exposures of environmentally induced epigenetic transgenerational inheritance.

The transgenerational disease phenotype investigated focused on pubertal onset and gonadal function. It was previously observed with vinclozolin induced transgenerational adult onset rat disease [2], the majority of disease developed between 6-12 months of age [6]. Therefore, additional adult onset diseases are anticipated as the animals age, but remain to be investigated. In regards to pubertal onset the plastics, low dose plastics, dioxin and hydrocarbon (jet fuel) exposures promoted an early (precocious) pubertal onset, FIG. 7, with no transgenerational effects on male pubertal onset. In the majority of developed countries early pubertal onset in girls has increased significantly in the past several decades [20,21]. This precocious puberty can promote behavioral, mental and endocrine physiological effects in the female and increase the incidence of adult onset disease [21]. Previous studies have suggested environmental exposures of estrogenic endocrine disruptors may be in part the causal factor for this pubertal onset condition. The current study extends this hypothesis to not only consider the direct exposures of the female, but ancestral exposures of the previous generations. The potential that early pubertal onset may in part involve epigenetic transgenerational inheritance mechanisms now needs to be considered.

In considering gonadal function and fertility both the testis and ovary were investigated. The testis was found to have an increased spermatogenic cell apoptosis in the jet fuel hydrocarbon F3 lineage males, FIG. 7. Previous observations with vinclozolin also showed a transgenerational spermatogenic cell apoptosis phenotype [2]. In many regions of the world human sperm numbers have declined [23] and male infertility has increased [24]. The potential that environmentally induced epigenetic transgenerational inheritance may be a factor in these disease conditions needs to be considered. In regards to ovarian function all the environmental exposures were found to promote a decline in total follicle numbers and specifically the primordial follicle pool size, FIG. 7. The primordial follicle pool size is the ovarian reserve for oocyte (egg) production throughout reproductive life [31]. The primordial follicle pool develops early in fetal (human) or early postnatal (rodent) life and then can not increase, but declines with age. Human females enter menopause when the primordial follicle pool is exhausted. A premature loss of follicles promotes infertility and is termed premature ovarian failure (POF), which is associated in part with the dramatic increase in female infertility in many parts of the world [25]. Previously it was hypothesized that POF was primarily of genetic origin, but the current study suggests environmental exposures and epigenetic transgenerational inheritance may also be a significant factor in the disease etiology to increase female infertility and premature onset of menopause. The environmental induction of the pubertal, testis and ovarian transgenerational disease phenotypes suggests that environmental epigenetics and epigenetic transgenerational inheritance will be molecular factors to consider in these and other disease etiologies.

The environmental compounds and mixtures used in the current study are all reported to be major exposures for the general population and military personnel. The ability of epigenetics to be involved in the long term and transgenerational actions of these exposures needs to be further investigated. The current study documents the distinct actions of each exposure to promote a unique sperm epigenome alteration, FIG. 8. Interestingly, these environmentally induced distinct epigenetic changes in differential DNA methylation regions (DMR) provide epigenetic biomarkers for ancestral environmental exposures. Each exposure had a distinct epigenetic signature that can be used as a biomarker. Although further research on individual animal variation, alterations in DMR in different cell types, and developmental effects on DMR are needed, the current study provides the proof of concept that epigenetic biomarkers for environmental exposures exist.

In addition to the identification of these ancestral epigenetic biomarkers in sperm, genomic features were identified that provide insight into why these sites may become permanently reprogrammed. A DNA sequence motif previously identified and termed "Environmentally Induced DNA Methylation Region 1 (EDM1)" [5] was found to be associated with a high percentage of the promoter regions of the hydrocarbon and dioxin exposure groups. Similar observations were previously made in examining the vinclozolin induced DMR in transgenerational sperm [5]. Interestingly, the plastics and pesticide exposure groups DMR did not have the presence of the EDM1 motif above background random promoter levels. Therefore, distinct molecular mechanisms may be involved in promoting the sensitivity of transgenerationally programmed DMR. This may include an alternate DNA sequence motif to be elucidated, or a more stochastic mechanism to be considered. The other genomic feature identified involved the CpG content or density associated with all the DMR's identified for all exposures. The DMR's identified had what is considered a low range CpG density [32] with a 1-8 CpG/100 bp content and no DMR with a CpG density greater than 15 CpG/100 bp, FIG. 11. Therefore, the DMR appear to have small clusters of CpG in a CpG desert, as previously described [33]. Evolutionarily CpG deserts develop due to the high mutation rate of CpG sites. The maintenance of small CpG clusters in these deserts may suggest a conserved critical epigenetic regulatory site. These genomic features are speculated to have a role in how the DMR become permanently programmed and promote epigenetic transgenerational inheritance. The current study focuses on a genome wide analysis of promoters.

The transmission of epigenetic information between generations in the absence of any direct environmental exposures is defined as epigenetic transgenerational inheritance [1, 2,3]. Therefore, in the case of exposure of a gestating female, only after the F3 generation can epigenetic transgenerational inheritance be considered [1]. The previous observations that vinclozolin and methyoxychlor induced epigenetic transgenerational inheritance [2] developed the question of compound specificity. The current study indicates different environmental compounds and mixtures with very different signal transduction processes involved can all promote epigenetic transgenerational phenotypes. Therefore, the specific compound or signaling event is not critical, but instead any agent that can modify the normal development and differentiation of the primordial germ cell during gonadal sex determination [1,3] can impact epigenetic programming and promote transgenerational inheritance. Although the majority of exposures will influence somatic cells and disease or phenotypes in the individual exposed, those actions that promote epigenetic transgenerational inheritance may have additional significant biological impacts. This includes providing a molecular mechanism for environmental toxicology, disease etiology, early life basis of adult onset disease [1,3] and evolutionary biology [34]. The availability of ancestral environmental epigenetic biomarkers is anticipated to significantly facilitate the research in these areas of science.

Material and Methods

Animal Studies

All experimental protocols for the procedures with rats were pre-approved by the Washington State University Animal Care and Use Committee (IACUC approval #02568-026). The University Department of Environmental Health and Safety approved all the protocols for the use of hazardous chemicals in this experiment. Hsd:Sprague Dawley®TMSD®™ female and male rats of an outbred strain (Harlan) at about 70 and 100 days of age were maintained in ventilated (up to 50 air exchanges/hour) isolator cages (cages with dimensions of 10¾" W×19¼" D×10¾" H, 143 square inch floor space, fitted in Micro-vent 36-cage rat racks; Allentown Inc., Allentown, N.J.) containing Aspen Sani chips (pinewood shavings from Harlan) as bedding, and a 14 h light: 10 h dark regimen, at a temperature of 70 F and humidity of 25% to 35%. The mean light intensity in the animal rooms ranged from 22 to 26 ft-candles. Rats were fed ad lib with standard rat diet (8640 Teklad 22/5 Rodent Diet; Harlan) and ad lib tap water for drinking. During the procedures, rats were held in an animal transfer station (AniGard 6VF, The Baker Company, Sanford, Me.) that provided an air velocity of about 0.5 inch.

At proestrus as determined by daily vaginal smears, the female rats, (90 days) were pair-mated with male rats (120 days). On the next day, the females were separated and their vaginal smears were examined microscopically and if they were sperm-positive (day 0) the rats were tentatively considered pregnant and then weighed with a digital animal weighing balance to monitor increases in body weight. Vaginal smears were continued for monitoring diestrus status in these rats until day 7. On embryonic day 7 (E-7) these females were weighed to determine if there was a significant increase in (greater than about 10 g) body weight, to confirm pregnancy in sperm-positive females. These pregnant rats were then given daily intraperitoneal injections of any one of the following single chemicals or mixtures with an equal volume of sesame oil (Sigma) on days E-8 through E-14 of gestation [35]. Treatment groups were Control, Pesticide (Permethrin+DEET), Plastics (Bisphenol-A, DBP and DEHP), Dioxin (TCDD), and Jet Fuel (JP8 hydrocarbon). The pregnant female rats treated with various mixtures were designated as the F0 generation. When there was a drop in the litter size and the sex ratio of pups in F1 generation of Plastics group, another treatment group was included with only half the dose of Bisphenol-A, DBP and DEHP and this group was designated 'Low Dose Plastics' group.

Breeding for F1, F2, and F3 Generations, Weaning Measures and Puberty Checks

The offspring of the F0 generation were the F1 generation. Likewise F2 and F3 generation offspring were generated. These rats were weaned from their mothers at 21 days of age. At weaning, the following weaning traits were measured; litter size, sex ratio, weaning weight (in grams), and anogenital index (AGI). Anogenital distance (AGD), was measured with a caliper that had an accuracy of $1/100^{th}$ of a mm. Males have a significantly higher AGD than that of females. Weaning weights of rats were measured by a digital balance. AGI was computed as the AGD in mm (from the bottom of the anal opening to the top of the genital opening) per gram of body weight at weaning. Starting at the age of 30 days for females and 35 days for males, puberty checks were performed. These checks were performed on a daily basis until puberty in each rat was confirmed. Onset of puberty for females was indicated by a clear vaginal opening, and for males it was indicated when the glans penis was able to fully extend free of the preputial fold (balano-preputial separation) [29].

Dissection of Rats for Tissue Collection

Both female and male rats of F1, F2 and F3 generation at 90-120 days of age were euthanized by $CO_2$ inhalation and cervical dislocation for dissection, collection and examination of tissues including testis, epididymis, and ovary. Body and tissue weights were measured at dissections. Blood samples were collected, allowed to clot, centrifuged and serum samples stored for hormone assays. Tissues were fixed in Bouins solution (Sigma) and 70% ethanol, then processed for paraffin embedding by standard procedures for histopathology examination. Five-micrometer sections were made and were either unstained or stained with H & E stain.

TUNEL Cell Death Assay

Testis sections were examined by Terminal deoxynucleotidyl transferase-mediated dUTP nick end labeling (TUNEL) assay (In situ cell death detection kit, Fluorescein, Roche Diagnostics, Mannheim, Germany) as per the manufacturer's protocols. The sections were deparaffinized in xylene, rehydrated through descending series of ethyl alcohols, deionized water and 1×PBS buffer. The sections were deproteinized by incubation at 37° C. in 250 ml of 1×PBS buffer containing 150 µl of Fungal Proteinase K (20 mg/ml; Invitrogen, Carlsbad, Calif.) and washed in 1×PBS buffer. About 20-25 µl of the enzyme-label solution mix was applied to testis sections. Slides were incubated at 37° C. for 90 min, washed in fresh 1×PBS buffer for 10 min, mounted with GVA mount and kept at 4° C. until examination. Testis sections were examined in a fluorescent microscope in dark to count the number of brightly fluorescing germ cells that are apoptotic.

Ovarian Analysis

Evaluation of Adult Ovaries: Ovaries taken from rats at the time of sacrifice were fixed, paraffin embedded and sectioned at 5 µm thickness. Every 30th section was collected and hematoxylin/eosin stained. The three stained sections (150 µm apart) through the central portion of the ovary with the largest cross-section were evaluated for number of primordial follicles, developing pre-antral follicles, small antral follicles, large antral follicles, small cystic structures and large cysts. The mean number of each evaluated structure per section was calculated across the three sections. Follicles had to be non-atretic and have the oocyte nucleus visible in the section in order to be counted. Primordial follicles had an oocyte surrounded by a single layer of either squamous or both squamous and cuboidal granulosa cells [36]. Developing pre-antral follicles had one or more complete layers of cuboidal granulosa cells. Small antral follicles had a fluid-filled antrum and a maximum diameter of 51 µm measured across the outermost granulosa cell layer. Large antral follicles had a diameter greater than 51 µm.

Sperm DNA Isolation and Methylated DNA Immunoprecipitation (MeDIP)

Sperm heads were separated from tails through sonication following previously described protocol (without protease inhibitors) [37] and then purified using a series of washes and centrifugations [38] from a total of nine F3 generation rats per treatment lineage that were 120 days of age. DNA extraction on the purified sperm heads was performed as previously described [5]. Equal concentrations of DNA from individual sperm samples were then used to produce pools of DNA material. Three DNA pools were produced in total per treatment, which contained the same amount of sperm DNA from three animals. Therefore a total of 45 animals were used for building three DNA pools per treatment for the 4 experimental groups plus controls. These DNA pools were then used for methylated DNA immunoprecipitation (MeDIP). MeDIP was performed as follows: 6 µg of genomic DNA was subjected to series of three 20 pulse sonications at 20% amplitude and the appropriate fragment size (200-1000 ng) was verified through 2% agarose gels; the sonicated genomic DNA was resuspended in 350 ul TE and denaturated for 10 min at 95° C. and then immediately placed on ice for 5 min; 100 ul of 5×IP buffer (50 mM Na-phosphate pH7, 700 mM NaCl, 0.25% Triton X-100) was added to the sonicated and denatured DNA. An overnight incubation of the DNA was performed with 5 ug of antibody anti-5-methylCytidine monoclonal from Diagenode S.A (Denville, N.J.) at 4° C. on a rotating platform. Protein A/G beads from Santa Cruz (Santa Cruz, Calif.) were prewashed on PBS-BSA 0.1% and resuspended in 40 ul 1×IP buffer. Beads were then added to the DNA-antibody complex and incubated 2 h at 4° C. on a rotating platform. Beads bound to DNA-antibody complex were washed 3 times with 1 ml 1×IP buffer; washes included incubation for 5 min at 4° C. on a rotating platform and then centrifugation at 6000 rpm for 2 min. Beads-DNA-antibody complex were then resuspended in 250 ul digestion buffer (50 mM Tris HCl pH 8, 10 mM EDTA, 0.5% SDS) and 3.5 ul of proteinase K (20 mg/ml) was added to each sample and then incubated overnight at 55° C. on a rotating platform. DNA purification was performed first with phenol and then with chloroform:isoamyl alcohol. Two washes were then performed with 70% ethanol, 1 M NaCl and glycogen. MeDIP selected DNA was then resuspended in 30 ul TE buffer.

Tilling Array MeDIP-Chip Analysis

Roche Nimblegen's Rat DNA Methylation 3×720K CpG Island Plus RefSeq Promoter Array was used, which contains three identical sub-arrays, with 720,000 probes per sub-array, scanning a total of 15,287 promoters (3,880 bp upstream and 970 bp downstream from transcription start site). Probe sizes range from 50-75 mer in length with the median probe spacing of 100 bp. Three different comparative (MeDIP vs MeDIP) hybridizations experiments were performed for each experimental group versus control, each encompassing DNA samples from 6 animals (3 treatment and 3 control groups) and 3 sub-arrays. MeDIP DNA samples from experimental groups were labeled with Cy3 and MeDIP DNA samples from the control group were labeled with Cy5.

Bioinformatic and Statistic Analyses of Chip Data

For each comparative hybridization experiment, raw data from both the Cy3 and Cy5 channels were imported into R(R Development Core Team (2010), R: A language for statistical computing, R Foundation for Statistical Computing, Vienna, Austria. ISBN 3-900051-07-0, URL http://www.R-project.org), checked for quality and converted to MA values (M=Cy5−Cy3; A=(Cy5+Cy3)/2). The following normalization procedure was conducted. Within each array, probes were separated into groups by GC content and each group was separately normalized, between Cy3 and Cy5 using the loess normalization procedure. This allowed for GC groups to receive a normalization curve specific to that group. After each array was normalized within array, the arrays were then normalized across arrays using the A quantile normalization procedure.

Following normalization each probe within each array was subjected to a smoothing procedure, whereby the probe's normalized M values were replaced with the median value of all probe normalized M values across all arrays within a 600 bp window. If the number of probes present in the window was less than 3, no value was assigned to that probe. Each probe's A values were likewise smoothed using the same procedure. Following normalization and smoothing each probe's M value represents the median intensity difference between vinclozolin generation and control generation of a 600 bp window. Significance was assigned to probe differences between treatment-generation samples and control generation samples by calculating the median value of the intensity differences as compared to a normal distribution scaled to the experimental mean and standard deviation of the normalized M. A Z-score and P-value were computed for each probe from that distribution. The statistical analysis was performed in pairs of comparative IP hybridizations between treatment lineage (T) and control lineage (C) (e.g. T1-C1 and T2-C2; T1-C1 and T3-C3; T2-C2 and T3-C3). In order to assure the reproducibility of the candidates obtained, only the candidates showing significant changes in every one of the paired comparisons were chosen as having a significant change in DNA methylation between each of the experimental group and controls. This is a very stringent approach to select for changes, since it only considers repeated changes in all paired analysis.

Clustered Regions of interest were then determined by combining consecutive probes within 600 bases of each other, and based on whether their mean M values were positive or negative, with significance p-values less than $10^{-5}$. The statistically significant differential DNA methylated regions were identified and P-value associated with each region presented. Each region of interest was then annotated for gene and CpG content. This list was further reduced to those regions with an average intensity value exceeding 9.5 (log scale) and a CpG density≥1 CpG/100 bp.

MeDIP-qPCR Confirmation

The MeDIP-Chip differential DNA methylation sites identified were further tested with a quantitative PCR analysis [39,40]. Real time qPCR quantification of each significant region obtained from the array was performed on MeDIP samples and the values were normalized to the DNA concentration of MeDIP samples measured by picogreen. These qPCR assays were optimized and performed by the Genomics Core Laboratory at the University of Arizona, Tucson, Ariz. Three technical replicates of Real Time qPCR reactions were performed for each one of three different MeDIPs per experimental group. Each MeDIP was from pools of sperm DNA samples from three animals. Ct values were obtained and the relative presence of specific DNA amplicons was calculated between control and exposure groups through the equation 'relative change=$2^{-\Delta Ct}$'. Statistical analysis between control and exposure groups was performed with student's t-test and changes with p<0.05 were considered significant.

Statistical Analysis

For statistical analysis, all the data on weaning traits and onset of puberty were averaged for each litter. These averages were used as input in the program GraphPad© Prism 5 statistical analysis program. One-way ANOVA or t-test were used to determine if the data on puberty, number of apoptotic germ cells, number of ovarian follicles from the individual treatment groups differ from those of Control groups with a probability of significance, p=0.05.

References for Example 2

1. Skinner M K, Manikkam M, Guerrero-Bosagna C (2010) Epigenetic transgenerational actions of environmental factors in disease etiology. Trends Endocrinol Metab 21: 214-222.
2. Anway M D, Cupp A S, Uzumcu M, Skinner M K (2005) Epigenetic transgenerational actions of endocrine disruptors and male fertility. Science 308: 1466-1469.
3. Jirtle R L, Skinner M K (2007) Environmental epigenomics and disease susceptibility. Nat Rev Genet. 8: 253-262.
4. Kavlock R, Cummings A (2005) Mode of action: inhibition of androgen receptor function—vinclozolin-induced malformations in reproductive development. Crit. Rev Toxicol 35: 721-726.
5. Guerrero-Bosagna C, Settles M, Lucker B J, Skinner M K (2010) Epigenetic transgenerational actions of vinclozolin on promoter regions of the sperm epigenome. PLoS ONE 5: e13100.
6. Anway M D, Leathers C, Skinner M K (2006) Endocrine disruptor vinclozolin induced epigenetic transgenerational adult-onset disease. Endocrinology 147: 5515-5523.
7. Waterland R A (2009) Is epigenetics an important link between early life events and adult disease? Horm Res 71 Suppl 1: 13-16.
8. Bruner-Tran K L, Osteen K G (2011) Developmental exposure to TCDD reduces fertility and negatively affects pregnancy outcomes across multiple generations. Reprod Toxicol 31: 344-350.
9. Salian S, Doshi T, Vanage G (2009) Impairment in protein expression profile of testicular steroid receptor coregulators in male rat offspring perinatally exposed to Bisphenol A. Life Sci 85: 11-18.
10. Stouder C, Paoloni-Giacobino A (2010) Transgenerational effects of the endocrine disruptor vinclozolin on the methylation pattern of imprinted genes in the mouse sperm. Reproduction 139: 373-379.
11. Pimentel D, Cooperstein S, Randell H, Filiberto D, Sorrentino S, et al. (2007) Ecology of Increasing Diseases: Population Growth and Environmental Degradation. Human Ecology 35: 653-668.
12. Talsness C E, Andrade A J, Kuriyama S N, Taylor J A, vom Saal F S (2009) Components of plastic: experimental studies in animals and relevance for human health. Philos Trans R Soc Lond B Biol Sci 364: 2079-2096.
13. Bernal A J, Jirtle R L (2010) Epigenomic disruption: the effects of early developmental exposures. Birth Defects Res A Clin Mol Teratol 88: 938-944.
14. Hunt P A, Susiarjo M, Rubio C, Hassold T J (2009) The bisphenol A experience: a primer for the analysis of environmental effects on mammalian reproduction. Biol Reprod 81: 807-813.
15. Kitchen L W, Lawrence K L, Coleman R E (2009) The role of the United States military in the development of vector control products, including insect repellents, insecticides, and bed nets. J Vector Ecol 34: 50-61.
16. Birnbaum L S, Fenton S E (2003) Cancer and developmental exposure to endocrine disruptors. Environ Health Perspect 111: 389-394.
17. Baccarelli A, Bollati V (2009) Epigenetics and environmental chemicals. Curr Opin Pediatr 21: 243-251.
18. Ritchie G, Still K, Rossi J, 3rd, Bekkedal M, Bobb A, et al. (2003) Biological and health effects of exposure to kerosene-based jet fuels and performance additives. J Toxicol Environ Health B Crit. Rev 6: 357-451.
19. Wong S S, Vargas J, Thomas A, Fastje C, McLaughlin M, et al. (2008) In vivo comparison of epithelial responses for S-8 versus JP-8 jet fuels below permissible exposure limit. Toxicology 254: 106-111.
20. DiVall S A, Radovick S (2009) Endocrinology of female puberty. Curr Opin Endocrinol Diabetes Obes 16: 1-4.
21. Traggiai C, Stanhope R (2003) Disorders of pubertal development. Best Pract Res Clin Obstet Gynaecol 17: 41-56.
22. Rockett J C, Lynch C D, Buck G M (2004) Biomarkers for assessing reproductive development and health: Part 1-Pubertal development. Environ Health Perspect 112: 105-112.
23. Fisher J S (2004) Environmental anti-androgens and male reproductive health: focus on phthalates and testicular dysgenesis syndrome. Reproduction 127: 305-315.
24. Hauser R, Sokol R (2008) Science linking environmental contaminant exposures with fertility and reproductive health impacts in the adult male. Fertil Steril 89: e59-65.
25. Vujovic S (2009) Aetiology of premature ovarian failure. Menopause Int 15: 72-75.
26. Kumar S (2004) Occupational exposure associated with reproductive dysfunction. J Occup Health 46: 1-19.
27. Hotchkiss A K, Lambright C S, Ostby J S, Parks-Saldutti L, Vandenbergh J G, et al. (2007) Prenatal testosterone exposure permanently masculinizes anogenital distance, nipple development, and reproductive tract morphology in female Sprague-Dawley rats. Toxicol Sci 96: 335-345.
28. Watanabe N, Kurita M (2001) The masculinization of the fetus during pregnancy due to inhalation of diesel exhaust. Environ Health Perspect 109: 111-119.
29. Engelbregt M J, Houdijk M E, Popp-Snijders C, Delemarre-van de Waal H A (2000) The effects of intra-uterine growth retardation and postnatal undernutrition on onset of puberty in male and female rats. Pediatr Res 48: 803-807.
30. Anway M D, Rekow S S, Skinner M K (2008) Transgenerational epigenetic programming of the embryonic testis transcriptome. Genomics 91: 30-40.
31. Skinner M K (2005) Regulation of primordial follicle assembly and development. Hum Reprod Update 11: 461-471.
32. Brinkman A B, Simmer F, Ma K, Kaan A, Zhu J, et al. (2010) Whole-genome DNA methylation profiling using MethylCap-seq. Methods 52: 232-236.
33. Covert T, Guerrero-Bosagna C, Hague M M, Settles M, Anway M, et al. (2011) Epigenetic Biomarkers Associated with the Transgenerational Actions of the Endocrine Disruptor Vinclozolin on Mouse Adult Onset Disease. (Submitted).
34. Crews D, Gore A C, Hsu T S, Dangleben N L, Spinetta M, et al. (2007) Transgenerational epigenetic imprints on mate preference. Proc Natl Acad Sci USA 104: 5942-5946.
35. Nilsson E E, Anway M D, Stanfield J, Skinner M K (2008) Transgenerational epigenetic effects of the endocrine disruptor vinclozolin on pregnancies and female adult onset disease. Reproduction 135: 713-721.
36. Meredith S, Dudenhoeffer G, Jackson K (2000) Classification of small type B/C follicles as primordial follicles in mature rats. J Reprod Fertil 119: 43-48.
37. Tateno H, Kimura Y, Yanagimachi R (2000) Sonication per se is not as deleterious to sperm chromosomes as previously inferred. Biol Reprod 63: 341-346.
38. Ward W S, Kimura Y, Yanagimachi R (1999) An intact sperm nuclear matrix may be necessary for the mouse paternal genome to participate in embryonic development. Biol Reprod 60: 702-706.
39. Martinato F, Cesaroni M, Amati B, Guccione E (2008) Analysis of Myc-induced histone modifications on target chromatin. PLoS ONE 3: e3650.
40. Sadikovic B, Yoshimoto M, Al-Romaih K, Maire G, Zielenska M, et al. (2008) In vitro analysis of integrated global high-resolution DNA methylation profiling with genomic imbalance and gene expression in osteosarcoma. PLoS ONE 3: e2834.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of detecting epimutations and regulatory sites of epimutations, comprising:

extracting genomic DNA from a biological sample;

sequencing said genomic DNA to obtain at least one genomic DNA sequence; and detecting a plurality of regions of said at least one genomic DNA sequence that contains one or both of epimutations and regulatory sites of epimutations by detecting each of i) and ii) using methylated DNA immunoprecipitation followed by a tiling array or next generation sequencing:

i) at least one DNA sequence region with a low density of CpG, wherein said low density of CpG is 10% or less CpG; and ii) at least one DNA sequence motif, wherein said at least one DNA sequence motif includes EDM2.

2. The method of claim 1, wherein said one or more regions of said at least one genomic DNA sequence are at least 400 base pairs long.

3. The method of claim 1, wherein said at least one DNA sequence motif includes EDM1.

4. The method of claim 1, wherein said at least one DNA sequence motif includes EDM1 and EDM2.

* * * * *

UNITED STATES PATENT AND TRADEMARK OFFICE
CERTIFICATE OF CORRECTION

PATENT NO. : 9,734,283 B2
APPLICATION NO. : 13/729175
DATED : August 15, 2017
INVENTOR(S) : Michael K. Skinner and Carlos M. Guerrero-Bosagna Page 1 of 1

It is certified that error appears in the above-identified patent and that said Letters Patent is hereby corrected as shown below:

In the Specification

Please insert the following paragraph in Column 1, beginning at Line 12:
--STATEMENT REGARDING FEDERALLY SPONSORED RESEARCH OR DEVELOPMENT
This invention was made with government support under grant no. R01 ES012974 awarded by National Institutes of Health and contract no. W81XWH-11-2-0027 awarded by the U.S. Army Medical Research and Materiel Command. The government has certain rights in the invention.--

Signed and Sealed this
Sixth Day of February, 2018

Joseph Matal
*Performing the Functions and Duties of the*
*Under Secretary of Commerce for Intellectual Property and*
*Director of the United States Patent and Trademark Office*